(12) United States Patent
Xie et al.

(10) Patent No.: US 11,087,864 B2
(45) Date of Patent: Aug. 10, 2021

(54) SYSTEMS AND METHODS FOR AUTOMATICALLY TAGGING CONCEPTS TO, AND GENERATING TEXT REPORTS FOR, MEDICAL IMAGES BASED ON MACHINE LEARNING

(71) Applicant: Petuum Inc., Pittsburgh, PA (US)

(72) Inventors: Pengtao Xie, Pittsburgh, PA (US); Eric Xing, Pittsburgh, PA (US)

(73) Assignee: PETUUM INC., Pittsburgh, PA (US)

( * ) Notice: Subject to any disclaimer, the term of this patent is extended or adjusted under 35 U.S.C. 154(b) by 233 days.

(21) Appl. No.: 16/207,117

(22) Filed: Dec. 1, 2018

(65) Prior Publication Data

US 2020/0027545 A1   Jan. 23, 2020

Related U.S. Application Data

(60) Provisional application No. 62/699,385, filed on Jul. 17, 2018, provisional application No. 62/756,024, filed on Nov. 5, 2018.

(51) Int. Cl.
*G16H 50/20* (2018.01)
*G16H 15/00* (2018.01)
(Continued)

(52) U.S. Cl.
CPC .............. *G16H 20/10* (2018.01); *G06F 16/36* (2019.01); *G06F 40/284* (2020.01); *G06K 9/46* (2013.01); *G06K 9/6228* (2013.01); *G06N 3/08* (2013.01); *G06N 20/00* (2019.01); *G06T 7/0012* (2013.01); *G16B 40/00* (2019.02); *G16H 10/60* (2018.01);
(Continued)

(58) Field of Classification Search
CPC ........ G16H 20/10; G16H 15/00; G16H 30/40; G16H 70/60; G16H 50/20; G16H 10/60; G16H 50/70; G06K 9/46; G06K 9/6228; G06K 9/628; G06K 9/726; G06K 2209/05; G06K 9/00979; G06K 9/6249; G06T 7/0012; G06T 2207/20081; G06T 2207/20084; G06N 3/08; G06N 20/00;
(Continued)

(56) References Cited

U.S. PATENT DOCUMENTS 10,224,119 B1   3/2019   Heinrich et al. ........ G16H 50/70
10,262,107 B1   4/2019   Tran et al. ............. G06F 19/326
(Continued)

FOREIGN PATENT DOCUMENTS

JP            2010-79930 A  *  4/2010   .............. G06Q 50/00

OTHER PUBLICATIONS

Machine translation of JP 2010-79930 A, Apr. 8, 2010. (Year: 2010).*

(Continued)

*Primary Examiner* — Andrew W Johns

(57) ABSTRACT

A system for assigning concepts to a medical image includes a visual feature module and a tagging module. The visual feature module is configured to obtain an image feature vector from the medical image. The tagging module is configured to apply a machine-learned algorithm to the image feature vector to assign a set of concepts to the image. The system may also include a text report generator that is configured to generate a written report describing the medical image based on the set of concepts assigned to the medical image.

19 Claims, 11 Drawing Sheets

(51) Int. Cl.

| | | |
|---|---|---|
| *G06K 9/46* | (2006.01) | |
| *G16H 20/10* | (2018.01) | |
| *G16H 10/60* | (2018.01) | |
| *G06N 20/00* | (2019.01) | |
| *G16B 40/00* | (2019.01) | |
| *G16H 70/60* | (2018.01) | |
| *G06N 3/08* | (2006.01) | |
| *G16H 30/40* | (2018.01) | |
| *G06K 9/62* | (2006.01) | |
| *G06T 7/00* | (2017.01) | |
| *G06F 16/36* | (2019.01) | |
| *H04L 29/08* | (2006.01) | |
| *G06F 40/284* | (2020.01) | |
| *G16H 50/70* | (2018.01) | |
| *G16B 50/00* | (2019.01) | |
| *G06K 9/72* | (2006.01) | |

(52) U.S. Cl.
CPC ............ *G16H 15/00* (2018.01); *G16H 30/40* (2018.01); *G16H 50/20* (2018.01); *G16H 70/60* (2018.01); *H04L 67/104* (2013.01); *G06K 9/628* (2013.01); *G06K 9/726* (2013.01); *G06K 2209/05* (2013.01); *G06T 2207/20081* (2013.01); *G06T 2207/20084* (2013.01); *G16B 50/00* (2019.02); *G16H 50/70* (2018.01)

(58) Field of Classification Search
CPC .... G06N 3/0445; G06N 3/0454; G06N 5/022; G16B 40/00; G16B 50/00; Y02A 90/10
See application file for complete search history.

(56) References Cited

U.S. PATENT DOCUMENTS

| | | | | |
|---|---|---|---|---|
| 10,496,884 | B1* | 12/2019 | Nguyen | G06N 3/0454 |
| 2005/0033606 | A1 | 2/2005 | Miller | 705/2 |
| 2005/0071194 | A1 | 3/2005 | Bormann et al. | 705/2 |
| 2006/0253441 | A1 | 11/2006 | Nelson | 707/7 |
| 2008/0085307 | A1 | 4/2008 | Sundharadas | 424/464 |
| 2011/0119212 | A1 | 5/2011 | De Bruin et al. | 706/12 |
| 2012/0330958 | A1 | 12/2012 | Xu et al. | 707/738 |
| 2014/0089000 | A1* | 3/2014 | Takata et al. | G16H 30/40 705/2 |
| 2016/0357929 | A1 | 12/2016 | Ghouri et al. | G06F 19/3431 |
| 2017/0154163 | A1 | 6/2017 | Jerby Arnon et al. | G06F 19/3437 |
| 2017/0193197 | A1 | 7/2017 | Randhawa et al. | G06F 19/363 |
| 2017/0228433 | A1 | 8/2017 | Gartrell et al. | G06F 17/30528 |
| 2017/0371623 | A1 | 12/2017 | Ross | G06F 7/58 |
| 2018/0060508 | A1 | 3/2018 | Fokoue-Nkoutche et al. | G06F 19/345 |
| 2018/0068089 | A1 | 3/2018 | Hu et al. | G06F 19/704 |
| 2018/0137244 | A1* | 5/2018 | Sorenson | G16H 30/20 |
| 2018/0196924 | A1 | 7/2018 | Assefa et al. | G06F 19/345 |
| 2018/0285679 | A1 | 10/2018 | Kmitay | G06K 9/4642 |
| 2018/0322249 | A1 | 11/2018 | Allen et al. | G06F 19/322 |
| 2019/0035496 | A1 | 1/2019 | Netzer et al. | G61H 20/10 |
| 2019/0114304 | A1 | 4/2019 | Oliveira et al. | G06F 16/93 |
| 2019/0392547 | A1* | 12/2019 | Katouzian | G06N 3/0445 |
| 2020/0013487 | A1 | 1/2020 | Luo et al. | G16H 10/20 |
| 2020/0219609 | A1* | 7/2020 | Harte | G06N 3/04 |
| 2020/0366495 | A1 | 11/2020 | Mahoney | H04L 9/3239 |

OTHER PUBLICATIONS

Gibbs sampling, May 2018, Wikipedia (Year: 2018).
Pengtao Xie, et al., "Diversit-Promoting Bayesian Learning of Latent Variable Models," International Conference on Machine Learning, vol. 48, pp. 1-10 (Year: 2016).
Shai Avidan, Joint Feature-basis subset selection, 2004, IEEE Computer Society (Year: 2004).

* cited by examiner

| Ground Truth | Ours-CoAttention | Ours-no-Attention | Soft Attention |
|---|---|---|---|
| No active disease. The heart and lungs have in the interval. Both lungs are clear and expanded. Heart and mediastinum normal. | No active disease. The heart and lungs have in the interval. Lungs are clear and expanded. Cardiomediastinal silhouette is within normal limits. No pleural effusion or pneumothorax is seen. No pleural effusion. No cavitary or pneumothorax. | The lungs are clear bilaterally. The are grossly normal. No focal lung consolidation. No acute bony abnormality. cm nodule within the right lower lobe on the lateral view. No pneumothorax or pleural effusion. No acute bony abnormality. The heart is not enlarged. The lungs are clear. No acute bony abnormality. | No acute cardiopulmonary abnormality. The lungs are clear bilaterally. Specifically no evidence of focal airspace consolidation pleural effusion or pneumothorax. Cardio mediastinal silhouette is unremarkable. Visualized osseous structures of the thorax are without acute abnormality. |
| No evidence of active disease. The lungs are clear. There is no focal airspace consolidation. No pleural effusion or pneumothorax. Heart size and mediastinal contour are wintihin normal limits. There are multilevel degenerative changes of the spine. | No acute cardiopulmonary findings. Heart size is not enlarged. No focal airspace consolidation suspicious pulmonary opacity large pleural effusion or pneumothorax. No focal areas of consolidation. Degererative changes of the spine. This is moderate exam of the hydropeumothorax. Lungs are clear. There is no focal airspace consolidation pleural effusion or pneumothorax. | The lungs are clear bilaterally. The are grossly normal. No pleural effusion. The heart is normal in size and contour. The lungs are clear. There are no acute bony findings. | No acute cardiopulmonary abnormality. The lungs are clear bilaterally. There is no pleural effusion or pneumothorax. The heart and mediastinum are normal. There is no focal air space opacity to suggest a pneumonia. |
| No acute cardiopulmonary abnormality. Normal heart size mediastinal contours. Eventration of the right hemidiaphargm. No focal airspace consolidation. No pleural effusion or pneumothorax. | No acute cardiopulmonary abnormality. Stable appearance of the thoracic aorta. The right lateral lower lobe is noted in the right lower right midlung. No large pleural effusion or focal airspace disease. Mild interstitial opacities. Atheroelectrotic calcification bony structures bilaterally. There is no pleural effusion or pneumothorax developed in the right lower lobe. | The lungs are clear bilaterally. The are grossly normal. No acute bony abnormality. The lungs are otherwise clear. No acute osseous abnormality. No acute osseous abnormality. The heart and mediastinum are normal. There is no focal air space opacity. | No acute cardiopulmonary abnormality. The lungs are clear bilaterally. There is no focal airspace consolidation. No pleural effusion or pneumothorax. Heart size and pulmonary vascularity appear within normal limits. |
| No acute cardiopulmonary abnormality. Heart size appears within normal limits. Pulmonary vasculature appears within normal limits. Overlying the middle cardiac silhouette representing a hiatal hernia. No focal consolidation pleural effusion or pneumothorax. No acute bony abnormality. | No active disease. The heart and lungs have in the interval. Nipple and lateral lucency in the lungs suggestive of focal airspace disease. The lungs are hyperexpanded consistent with emphysema in the left lower lobe. This is most at the upper lobes. This may indicate hypoventilated irregularities or effusions. The lungs are otherwise grossly clear. Resolution of by normal pleural effusion. | No acute cardiopulmonary abnormality. The lungs are clear bilaterally. The are grossly normal. No focal airspace consolidation. No pneumothorax or pleural effusion. Heart size and pulmonary vascularity within normal limits. There is no pneumothorax or pleural effusion. | No acute cardiopulmonary abnormality. There is no focal airspace consolidation. No pneumothorax or pleural effusion. No acute bony abnormality. Heart size is normal. |

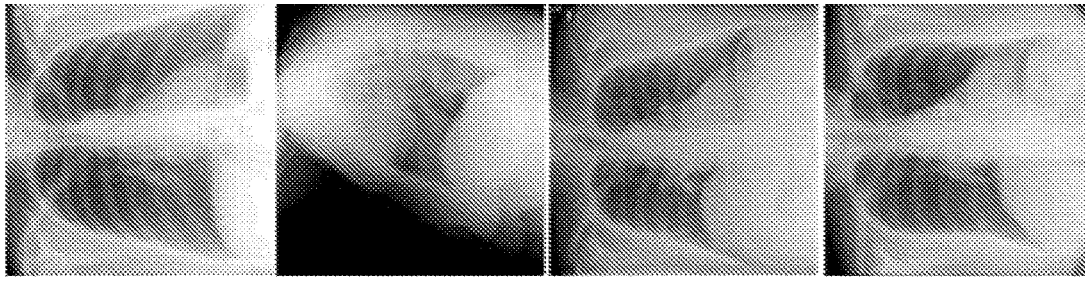

FIG. 8

SYSTEMS AND METHODS FOR AUTOMATICALLY TAGGING CONCEPTS TO, AND GENERATING TEXT REPORTS FOR, MEDICAL IMAGES BASED ON MACHINE LEARNING

CROSS-REFERENCE TO RELATED APPLICATION(S)

This application claims the benefit of and priority to 1) U.S. Provisional Patent Application Ser. No. 62/699,385, filed Jul. 17, 2018, for "Diversity-Promoting and Large-Scale Machine Learning for Healthcare", and 2) U.S. Provisional Patent Application Ser. No. 62/756,024, filed Nov. 5, 2018, for "Diversity-Promoting and Large-Scale Machine Learning for Healthcare", the entire disclosures of which are incorporated herein by references.

This application has subject matter in common with: 1) U.S. patent application Ser. No. 16/038,895, filed Jul. 18, 2018, for "A Machine Learning System for Measuring Patient Similarity", 2) U.S. patent application Ser. No. 15/946,482, filed Apr. 5, 2018, for "A Machine Learning System for Disease, Patient, and Drug Co-Embedding, and Multi-Drug Recommendation", 3) U.S. patent application Ser. No. 16/207,114, filed Dec. 1, 2018, for "Systems and Methods for Predicting Medications to Prescribe to a Patient Based on Machine Learning", 4) U.S. patent application Ser. No. 16/207,115, filed Dec. 1, 2018, for "Systems and Methods for Medical Topic Discovery Based on Large-Scale Machine Learning", 5) U.S. patent application Ser. No. 16/207,119, filed Dec. 1, 2018, for "Systems and Methods for Automatically Generating International Classification of Disease Codes for a Patient Based on Machine Learning", the entire disclosures of which are incorporated herein by reference, and the entire disclosures of which are incorporated herein by reference.

TECHNICAL FIELD

The present disclosure generally relates to machine learning for healthcare, and more particularly, to systems and methods that apply machine learning algorithms to medical images to automatically tag concepts to the images and generate corresponding text reports for the images.

BACKGROUND

With the widespread adoption of electronic health records (EHR) systems, and the rapid development of new technologies such as high-throughput medical imaging devices, low-cost genome profiling systems, networked and even wearable sensors, mobile applications, and rich accumulation of medical knowledge/discoveries in databases, a tsunami of medical and healthcare data has emerged. It was estimated that 153 exabytes (one exabyte equals one billion gigabytes) of healthcare data were produced in 2013. In 2020, an estimated 2314 exabytes will be produced. From 2013 to 2020, an overall rate of increase is at least 48 percent annually.

In addition to the sheer volume, the complexity of healthcare data is also overwhelming. Such data includes clinical notes, medical images, lab values, vital signs, etc., coming from multiple heterogeneous modalities including texts, images, tabular data, time series, graph and so on. The rich clinical data is becoming an increasingly important source of holistic and detailed information for both healthcare providers and receivers. Collectively analyzing and digesting these rich information generated from multiple sources; uncovering the health implications, risk factors, and mechanisms underlying the heterogeneous and noisy data records at both individual patient and whole population levels; making clinical decisions including diagnosis, triage, and treatment thereupon, are now routine activities expected to be conducted by medical professionals including physicians, nurses, pharmacists and so on.

As the amount and complexity of medical data are rapidly growing, these activities are becoming increasingly more difficult for human experts. The information overload makes medical analytics and decisions-making time consuming, error-prone, suboptimal, and less-transparent. As a result, physicians, patients, and hospitals suffer a number of pain points, quality-wise and efficiency-wise. For example, in terms of quality, 250,000 Americans die each year from medical errors, which has become the third leading cause of death in the United States. Twelve million Americans are misdiagnosed each year. Preventable medication errors impact more than 7 million patients and cost almost $21 billion annually. Fifteen to twenty-five percent of patients are readmitted within 30 days and readmissions are costly (e.g., $41.3 billion in 2011). In terms of inefficiency, patients wait on average 6 hours in emergency rooms. Nearly 400,000 patients wait 24 hours or more. Physicians spend only 27 percent of their office day on direct clinical face time with patients. The U.S. healthcare system wastes $750 billion annually due to unnecessary services, inefficient care delivery, excess administrative costs, etc.

The advancement of machine learning (ML) technology opens up opportunities for next generation computer-aided medical data analysis and data-driven clinical decision making, where machine learning algorithms and systems can be developed to automatically and collectively digest massive medical data such as electronic health records, images, behavioral data, and the genome, to make data-driven and intelligent diagnostic predictions. An ML system can automatically analyze multiple sources of information with rich structure; uncover the medically meaningful hidden concepts from low-level records to aid medical professionals to easily and concisely understand the medical data; and create a compact set of informative diagnostic procedures and treatment courses and make healthcare recommendations thereupon.

It is therefore desirable to leverage the power of machine learning in automatically distilling insights from large-scale heterogeneous data for automatic smart data-driven medical predictions, recommendations, and decision-making, to assist physicians and hospitals in improving the quality and efficiency of healthcare. It is further desirable to have machine learning algorithms and systems that turn the raw clinical data into actionable insights for clinical applications. One such clinical application relates to describing medical images either in the form of word tagging or text report generation.

When applying machine learning to healthcare application, several fundamental issues may arise, including:

1) How to better capture infrequent patterns: At the core of ML-based healthcare is to discover the latent patterns (e.g., topics in clinical notes, disease subtypes, phenotypes) underlying the observed clinical data. Under many circumstances, the frequency of patterns is highly imbalanced. Some patterns have very high frequency while others occur less frequently. Existing ML models lack the capability of capturing infrequent patterns. Known convolutional neural network do not perform well on infrequent patterns. Such a deficiency of existing models possibly results from the design of their objective function used for training. For example, a maximum likelihood estimator would reward itself by modeling the frequent patterns well as they are the major contributors to the likelihood function. On the other hand, infrequent patterns contribute much less to the likelihood, thereby it is not very rewarding to model them well and they tend to be ignored. Infrequent patterns are of crucial importance in clinical settings. For example, many infrequent diseases are life-threatening. It is critical to capture them.

2) How to alleviate overfitting: In certain clinical applications, the number of medical records available for training is limited. For example, when training a diagnostic model for an infrequent disease, typically there is no access to a sufficiently large number of patient cases due to the rareness of this disease. Under such circumstances, overfitting easily happens, wherein the trained model works well on the training data but generalizes poorly on unseen patients. It is critical to alleviate overfitting.

3) How to improve interpretability: Being interpretable and transparent is a must for an ML model to be willingly used by human physicians. Oftentimes, the patterns extracted by existing ML methods have a lot of redundancy and overlap, which are ambiguous and difficult to interpret. For example, in computational phenotyping from EHRs, it is observed that the learned phenotypes by the standard matrix and tensor factorization algorithms have much overlap, causing confusion such as two similar treatment plans are learned for the same type of disease. It is necessary to make the learned patterns distinct and interpretable.

4) How to compress model size without sacrificing modeling power: In clinical practice, making a timely decision is crucial for improving patient outcome. To achieve time efficiency, the size (specifically, the number of weight parameters) of ML models needs to be kept small. However, reducing the model size, which accordingly reduces the capacity and expressivity of this model, typically sacrifice modeling power and performance. It is technically appealing but challenging to compress model size without losing performance.

5) How to efficiently learn large-scale models: In certain healthcare applications, both the model size and data size are large, incurring substantial computation overhead that exceeds the capacity of a single machine. It is necessary to design and build distributed systems to efficiently train such models.

Tagging of Medical Images

Medical images generated from radiography, computed tomography (CT) scans, magnetic resonance imaging (MRI), ultrasound, biopsy etc. are widely used in hospitals and clinics for diagnosis, treatment, and surgery. Once read, these images are dumped into the picture archiving and communication system. Lacking accurate and rich textual labels, these images are difficult to index and search. As a result, the utilization of these images is under-explored.

It is therefore desirable to automatically tagging clinical images with medical concepts so that accessibility to images is improved and physicians can search images using keywords. Doing so, however, is challenging. First, a medical image usually contains rich information. As a result, it can be simultaneously tagged with multiple concepts. For example, with reference to FIG. 11A, an image may be tagged with "capillary", "fibroblast", and "mononuclear". These concepts have strong clinical or biological correlations. For example, mononuclear cell and fibroblast have an interaction in scleroderma. Capillaries and fibroblast have a dynamic interaction in the heart. Such correlations can be explored to improve tagging accuracy. Here is an example. Since capillary is visually similar to Mallory bodies, it is difficult to distinguish these two based on image features. But Mallory bodies have little correlation with fibroblast and mononuclear cell. Leveraging the concept-correlations, we can correctly choose capillary rather than Mallory body as the label. Technically, how to capture these correlations is nontrivial.

Second, medical concepts are usually organized by physicians into a hierarchical ontology. On the top of the hierarchy are general concepts. From top to bottom, each concept is divided into more fine-grained sub-concepts. With reference to FIG. 11B, which illustrates an example hierarchy tree, each node represents a disease, whose children represent subtypes of this disease. For instance, meningomyelocele and anencephaly are both subtypes of neural tube defects. This hierarchical structure can be leveraged to improve tagging accuracy. On one hand, if A and B are both children of C, then it is unlikely to use A and B to simultaneously tag an image. For instance, low power microscopic, middle power microscopic, and high power microscopic are children of microscopic. A pathology image can only be taken by one of these microscopic techniques. On the other hand, if the distance between A and B in the concept tree is smaller than that between A and C and we know A is the correct label, then B is more likely to be the correct label than C, since concepts with smaller distance are more relevant. For example, abscess is closer to phagocytosis than omphalocele. The former two are both under the sub-tree rooted with inflammation. As a result, if an image is tagged with abscess, it is more likely to be tagged with phagocytosis than omphalocele. How to explore the hierarchical structure among concepts for better tagging is technically demanding.

Third, in images showing abnormalities, the abnormal regions are usually very small, occupying a small proportion of the entire image. As shown in FIG. 11C, the dark round areas (marked with contours) show lymph nodes which are involved by the neoplasm. It is difficult to tag these abnormalities because of the smallness of the abnormal regions. How to detect these regions and properly tag them is challenging.

Text Report Generation for Medical Images

Medical images, such as radiology and pathology images, are widely used in hospitals and clinics for the diagnosis and treatment of many diseases. The reading and interpretation of medical images are usually conducted by specialized medical professionals. They write textual reports to narrate the findings regarding each area of the body examined in the imaging study, specifically whether each area was found to be normal, abnormal or potentially abnormal.

For less-experienced radiologists and pathologists, especially those working in the rural area where the quality of healthcare is relatively low, writing medical-imaging reports is demanding. For experienced radiologists and pathologists, writing imaging reports is tedious and time consuming. In nations with a large population such as China, a radiologist may need to read hundreds of radiology images per day. Typing the findings of each image into the computer takes about 5-10 minutes, which occupies most of their working time. In sum, for both unexperienced and experienced medical professionals, writing imaging reports is unpleasant.

It is therefore desirable to automatically generate medical image reports. In order to do so, however, several challenges need to be addressed. First, a complete diagnostic report is comprised of multiple heterogeneous forms of information, including sentences, paragraphs, and keywords. Generating this heterogeneous information in a unified framework is technically demanding. Secondly, an imaging report usually focuses more on narrating the abnormal findings since they directly indicate diseases and guide treatment. How to localize image-regions that contain abnormalities and attach the right description to them are challenging. Third, the descriptions in imaging reports are usually long, containing multiple sentences or even multiple paragraphs. Generating such long text is highly nontrivial.

SUMMARY

In one aspect of the disclosure, a method of assigning concepts to a medical image includes obtaining an image feature vector from the medical image, and applying a machine-learned algorithm to the image feature vector to assign a set of concepts to the image. The method may further include generating a written report describing the medical image based on the set of concepts assigned to the medical image.

In another aspect of the disclosure, a system for assigning concepts to a medical image includes a visual feature module and a tagging module. The visual feature module is configured to obtain an image feature vector from the medical image. The tagging module is configured to apply a machine-learned algorithm to the image feature vector to assign a set of concepts to the image. The system may also include a text report generator that is configured to generate a written report describing the medical image based on the set of concepts assigned to the medical image.

In another aspect of the disclosure, a machine learning apparatus for generating a map between medical image concepts and medical images includes a processor and a memory coupled to the processor. The processor is configured to generate representations of medical images in a form of image feature vectors, and generate representations of concepts describing medical images in a form of concept vectors. The processor is further configured to process the image feature vectors and the concept vectors to obtain measures of relevance between images and concepts and measures of correlation among different concepts, and to associate each medical image represented in the image feature vector with one or more concepts represented in the concept vector based on the measures of relevance and the measures of correlation.

It is understood that other aspects of methods and systems will become readily apparent to those skilled in the art from the following detailed description, wherein various aspects are shown and described by way of illustration.

BRIEF DESCRIPTION OF THE DRAWINGS

Various aspects of apparatuses and methods will now be presented in the detailed description by way of example, and not by way of limitation, with reference to the accompanying drawings, wherein:

FIG. 8 are illustrations of examples of text reports generated by a trained text report generation module.

DETAILED DESCRIPTION

Disclosed herein is a system for automatically associating descriptive text or words with a medical image. The text or words are generally referred to herein as concepts, labels or tags, while the association of these concepts, labels or tags to an image is referred to as tagging. In one embodiment, the system processes an input medical image to obtain a representation of images features or contextual features, and applies a machine-learned algorithm to the representation to identify concepts to tag to the medical image. In another embodiment, the machine-learned algorithm automatically generates a written diagnostic report for a medical image based on the concepts that are tagged to the medical image. Some of the concepts and features described herein are included in Diversity-promoting and Large-scale Machine Learning for Healthcare, a thesis submitted by Pengtao Xie in August 2018 to the Machine Learning Department, School of Computer Science, Carnegie Mellon University, which is hereby incorporated by reference in its entirety.

Figure 1:
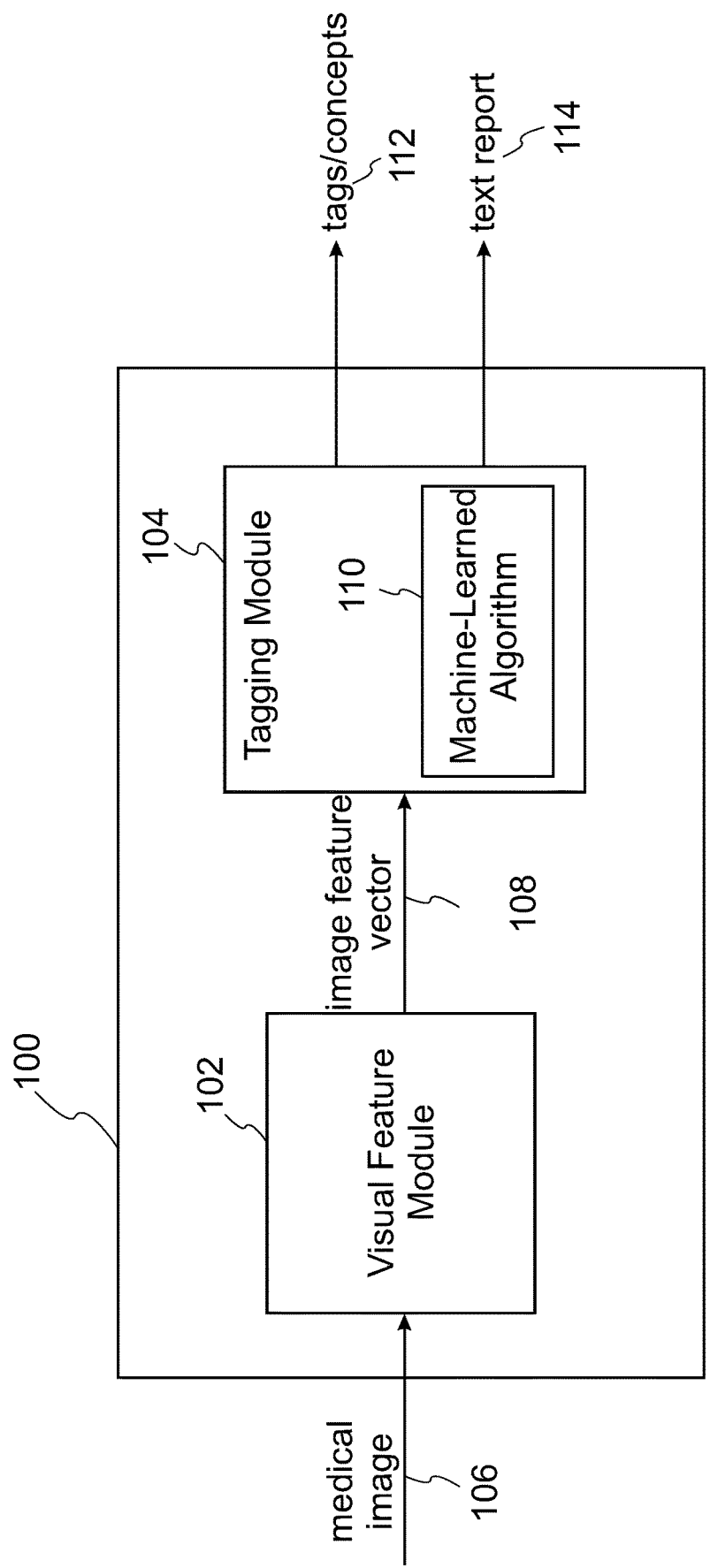
FIG. 1 is a block diagram of a system for automatically tagging concepts to medical images and generating corresponding text reports for the images using a machine-learned algorithm.

With reference to FIG. 1, a medical image tagging system 100 includes a visual feature module 102 (also referred to as a contextual attention encoding module) and a tagging module 104. The visual feature module 102 is configured to receive a medical image 106 and to produce a representation of the image as an image feature vector 108. The tagging module 104 receives the representation of the image as an image feature vector 108 and applies a previously-trained machine-learned algorithm 110 to the vector. The algorithm 110 determines relevant tags corresponding to the image features included in the image feature vector 108 and outputs one or more tags 112 that describe the image. The algorithm may also process the tags to generate a written text report 114.

Figure 2:
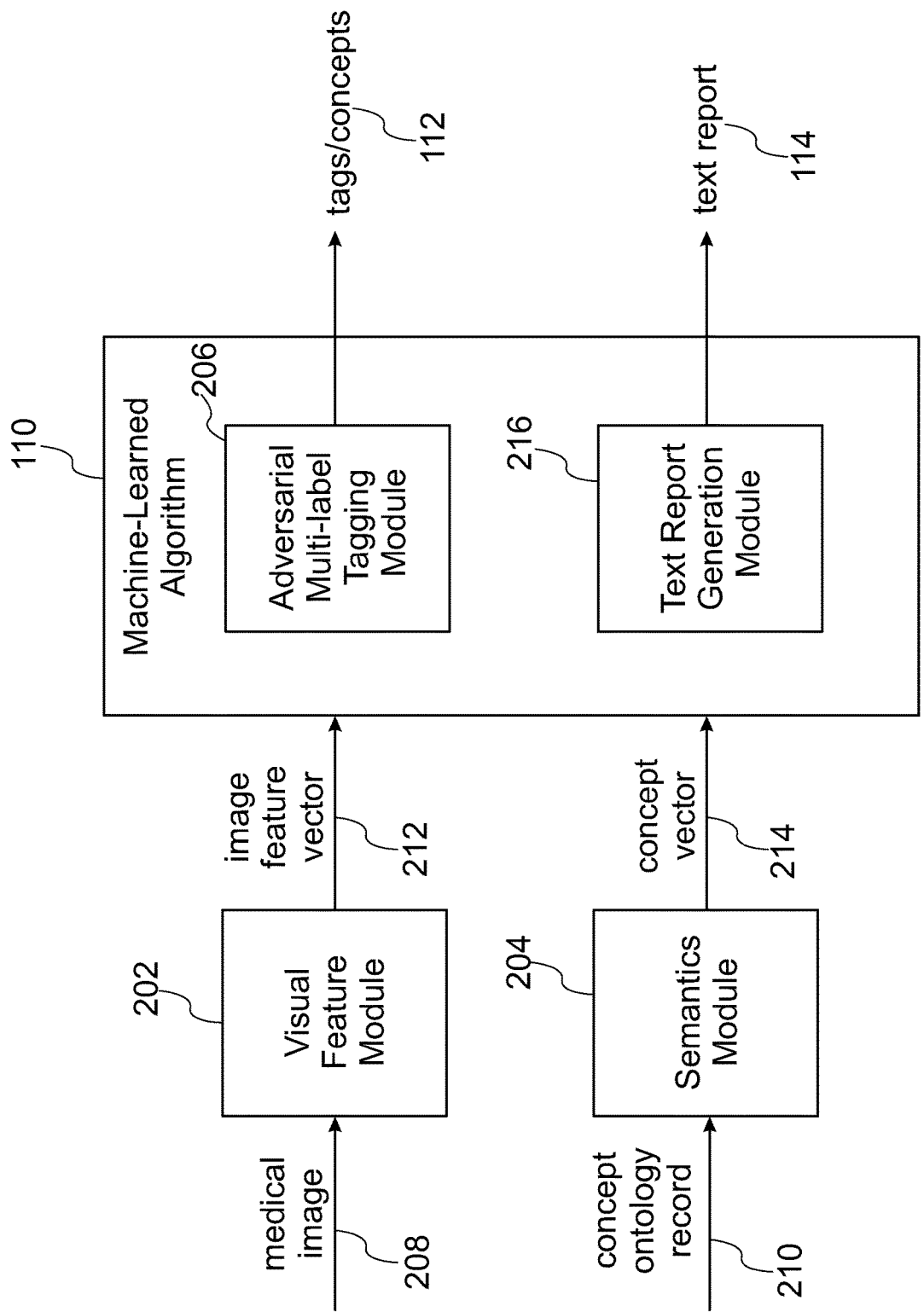
FIG. 2 is a block diagram of a model used to develop and train the machine-learned algorithm of FIG. 1.

With reference to FIG. 2, the machine-learned algorithm 110 of the tagging module 104 of FIG. 1 is designed and trained using a model that consists of four modules: a visual feature module 202 (also referred to as a contextual attention encoding module), a semantics module 204 (also referred to as tree-of-sequences LSTM encoder), an adversarial multi-label tagging module 206, and an optional text report generation module 216. The inputs to the model include a medical image 208 and an ontology of medical concepts 210. As used herein, an ontology is a set of concepts that describe one or more medical features or characteristics apparent in a medical image. The outputs of the model include a set of concepts or tags 112 that are determined by a machine-learned algorithm to describe the medical image and/or a text report 114 that describes the medical image. In one configuration, in the concept ontology 210, only the leaf nodes are used for tagging.

The visual feature module 202 takes the medical image 208 as input, localizes abnormal regions which are given higher importance weights, and generates a weighted representation for this image as an image feature vector 212. The semantics module 204 takes the concept ontology 210 as input, uses sequential LSTMs to encode individual concepts and utilizes a bidirectional tree-structured LSTM to incorporate the hierarchical relationship among concepts into their representations and generates a concept vector 214. The adversarial multi-label tagging module 206 takes the representations of the image 212 and the representation of the concepts 214 as inputs, incorporates label-correlations using adversarial learning, and outputs multiple concepts to tag to the input medical image 208. The visual feature module 202 used to develop and train the machine-learned algorithm 110 is configured to generate representations of images in the same way as the visual feature module 102 of the medical image tagging system 100 of FIG. 1.

Visual Feature Module (Contextual Attention Encoder)

When reading a medical image, physicians care more about the regions that show abnormalities. These abnormalities are usually indicators of diseases and prompt the physicians to take treatment actions. The abnormal regions are usually small, which are difficult to detect and tag. It is important to localize these regions and encourage the tagging module 206 to pay more attention to them.

The abnormal regions can be spotted by comparing them with their context—the entire image. It is often the case that a majority of an image contains normal tissues, whose visual appearance differs from the abnormalities. Informed by this, the visual feature module 202, i.e., contextual attention encoder, is configured to calculate the level of abnormality in each region by contrasting that region with the entire image.

Figure 3:
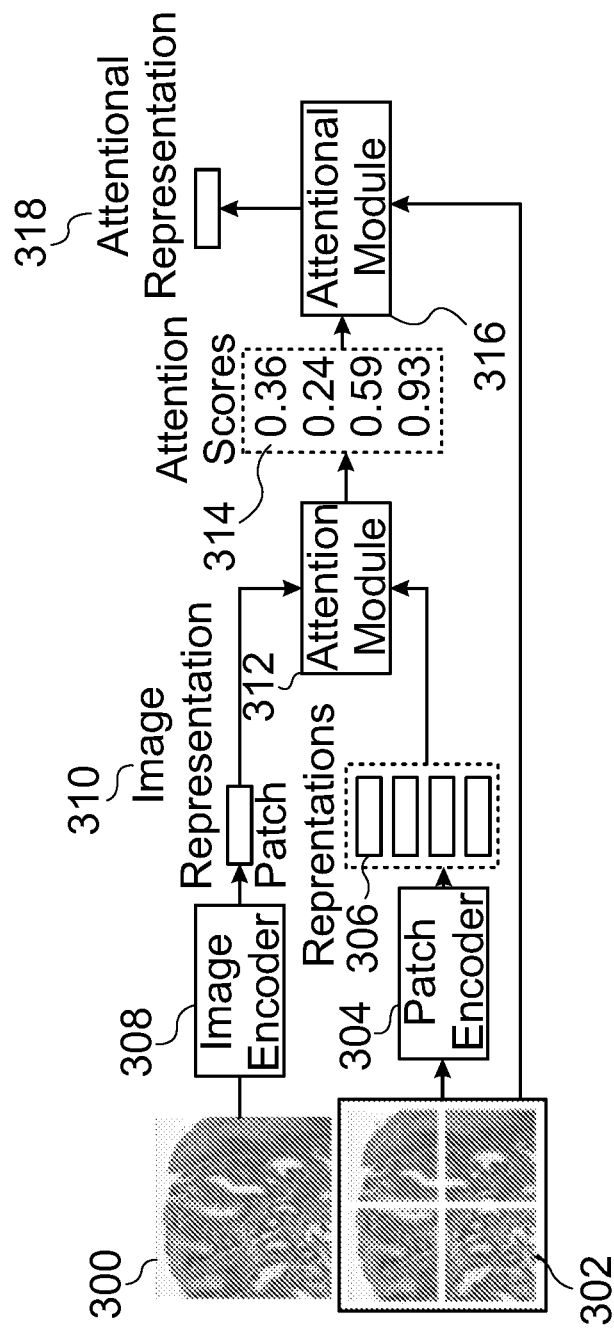
FIG. 3 is a block diagram of image processing performed by a visual feature module included in the model of FIG. 2.

FIG. 3 is an illustration of image processing performed by the visual feature module 202. The visual feature module 202 divides the input image 300 into regions or patches 302 and applies a convolutional neural network (CNN) to the patches to learn visual features for these patches. While only four patches 302 are shown in FIG. 3, the visual feature module 202 may divide the input image into more patches. For each patch 302, a patch encoder 304 extract a representation 306 of that patch. For the entire image 300 (which is deemed as context), an image encoder 308 is used to capture the holistic information of this image. For each patch 302, its representation 306 and the image representation 310 are concatenated and fed into an attention module 312 which generates an attention score 314 indicating how abnormal the particular patch is. The attention scores 314 are used to weight pixels. The weighted pixels are fed into an attentional encoder 316 to generate an attentional representation 318 for this image 300. For simplicity, the patches 302 are assumed to nonoverlap, hence each pixel belongs to exactly one patch.

Figure 4:
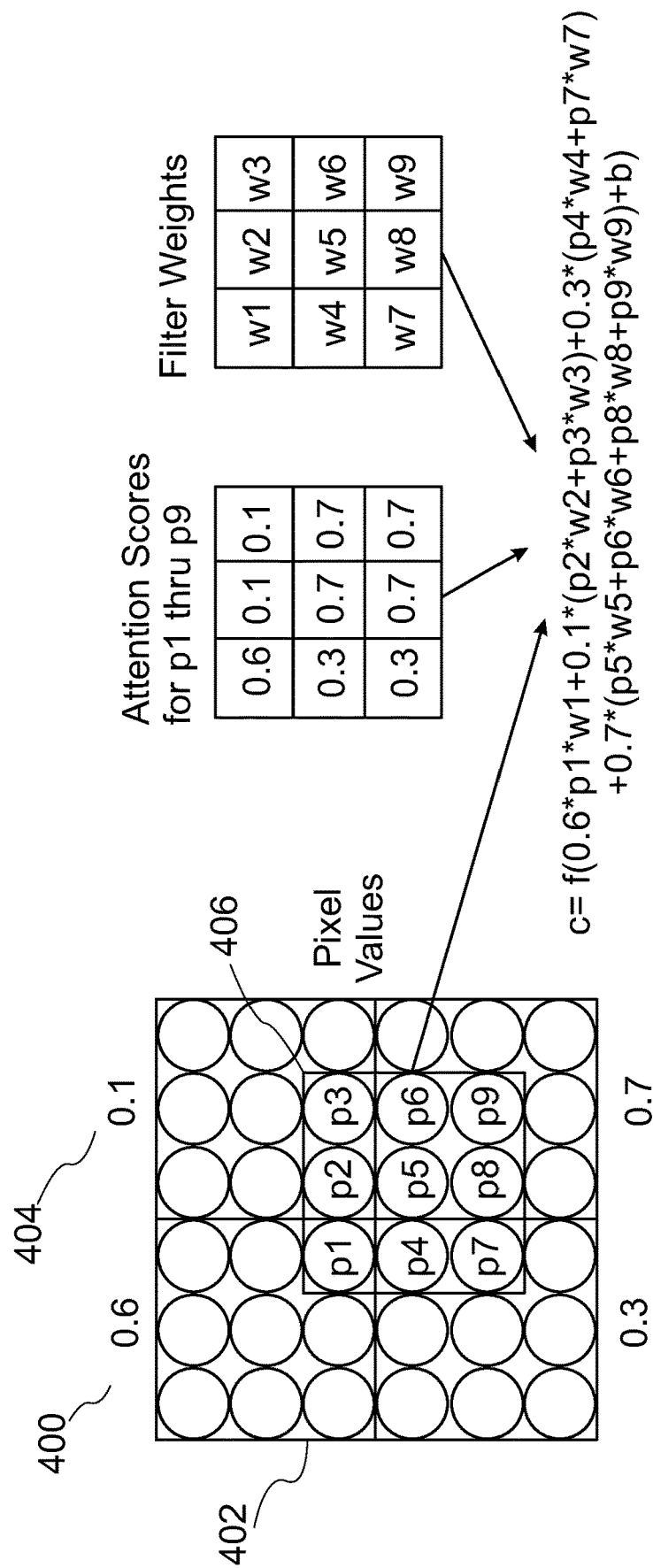
FIG. 4 is a block diagram of a weighting function included in the image processing of FIG. 3.

The value of a pixel is weighted by the attention score 314 of the patch containing it. In the attentional encoder 316, attentional convolution is performed, whereby the filters take weighted pixels as inputs to calculate the feature map. FIG. 4 illustrates and example of the weighting process. The 6 pixel×6 pixel image 400 image is divided into 4 patches 402, having respective attention scores 404 of 0.6, 0.1, 0.3, and 0.7. When a 3 pixel×3 pixel filter 406 is applied, each pixel in the receptive field is weighted using the attention score of the patch 402 containing this pixel. Then the convolution is performed between the weighted pixels and the filter weights, by calculating the following equation:

$$c = f(\Sigma_{i=1}^{n} a_i p_i w_i + b) \qquad \text{(Eq. 1)}$$

where $\{a_i\}$ are the attention scores, $\{p_i\}$ are the pixel values, and $\{w_i\}$ are the weights of filters. Extending the method to overlapped patches is straightforward: the weight of a pixel is calculated by averaging the attention scores of overlapping patches that contain this pixel.

Semantics Module (Tree-of-Sequences LSTM Encoder)

The semantics module 204, which may be configured as a multi-label classification (MLC) network, predicts tags in the form of keywords lists that are relevant to the visual features, and thus relevant to the image. In the tag vocabulary, each tag is represented by a word-embedding vector. Given the predicted tags for a specific image, their word-embedding vectors are retrieved to serve as the semantic features of this image.

Figure 5:
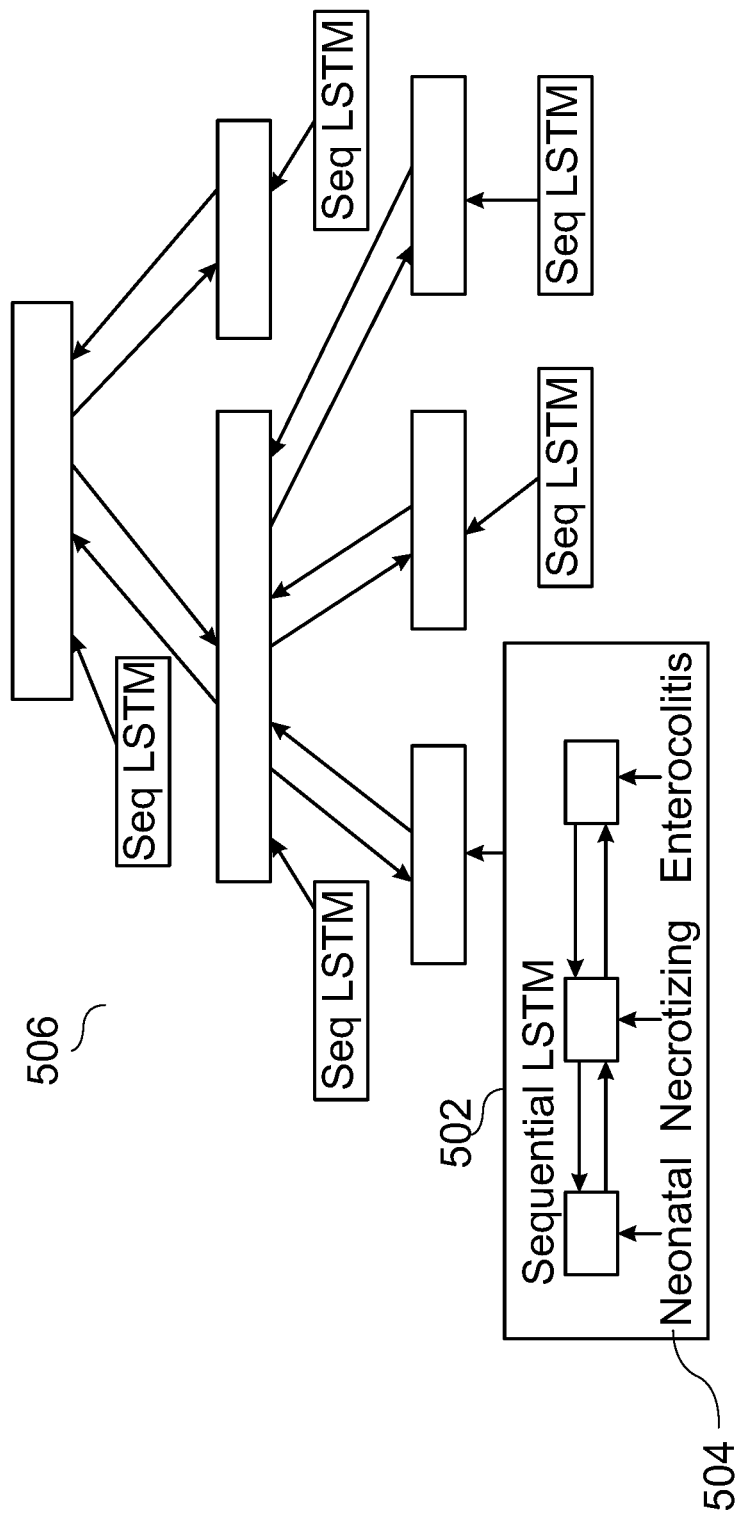
FIG. 5 is an illustration of an hierarchy structure of a tree-of-sequences long short-term memory (LSTM) used by a semantics module included in the model of FIG. 2.

With reference to FIG. 5, the semantics module 204 employs a sequential LSTM (SLSTM) 502 to learn embedding vectors for medical concepts. Each concept has a name (a sequence of words 504) that tells the semantics of this concept. A sequential LSTM (SLSTM) 502 is used to capture the semantics of words and the sequential structure among words and to encode this concept/name. Meanwhile, in the hierarchical ontology, the concepts possess hierarchical relationships. To capture such relationships, on top of the encodings generated by the SLSTMs 502, a tree LSTM (TLSTM) 506 is built along the hierarchy, ending up with a tree-of-sequences LSTM model. The encodings produced by the SLSTMs 502 are the inputs of the TLSTM.

Sequential LSTM: A SLSTM network is a special type of recurrent neural network that (1) learns the latent representation (which usually reflects certain semantic information) of words; (2) models the sequential structure among words. In the word sequence, each word t is allocated with an SLSTM unit, which consists of the following components: input gate $i_t$, forget gate $f_t$, output gate $o_t$, memory cell $c_t$, and hidden state $s_t$. These components (vectors) are computed as follows:

$$i_t = \sigma(W^{(i)} s_{t-1} + U^{(i)} x_t + b^{(i)})$$

$$f_t = \sigma(W^{(f)} s_{t-1} + U^{(f)} x_t + b^{(f)})$$

$$o_t = \sigma(W^{(o)} s_{t-1} + U^{(o)} x_t + b^{(o)})$$

$$c_t = i_t \odot \tan h(W^{(c)} s_{t-1} + U^{(c)} x_t + b^{(c)}) + f_t \odot c_{t-1}$$

$$s_t = o_t \odot \tan h(c_t), \qquad \text{(Eq. 2)}$$

where $x_t$ is the embedding vector of word t. W, U are component-specific weight matrices and b are bias vectors.

Tree-of-sequences LSTM: A bi-directional tree LSTM (TLSTM) captures the hierarchical relationships among code. The inputs of this TLSTM include the code hierarchy and the hidden states of individual codes produced by the SLSTMs. It consists of a bottom-up TLSTM and a top-down TLSTM, which produce two hidden states $h\!\uparrow$ and $h\!\downarrow$ at each node in the tree.

In the bottom-up TLSTM, an internal node (representing a code C, having M children) is comprised of the following components: an input gate $i\!\uparrow$, an output gate $o\!\uparrow$, a memory cell $c\!\uparrow$, a hidden state $h_\uparrow$, and M child-specific forget gates $\{f_\uparrow^{(m)}\}_{m=1}^M$ where $f_\uparrow^{(m)}$ corresponds to the m-th child. The transition equations among components are:

$$i_\uparrow = \sigma(\Sigma_{m=1}^M(W_\uparrow^{(i,m)} h_\uparrow^{(m)} + U^{(i)}s + b_\uparrow^{(i)})$$

$$\forall m, f_\uparrow^{(m)} = \sigma(W_\uparrow^{(f,m)} h_\uparrow^{(m)} + U^{(f,m)}s + b_\uparrow^{(f,m)})$$

$$o_\uparrow = \sigma(\Sigma_{m=1}^M(W_\uparrow^{(o,m)} h_\uparrow^{(m)} + U^{(o)}s + b_\uparrow^{(o)})$$

$$u_\uparrow = \tan h(\Sigma_{m=1}^M(W_\uparrow^{(u,m)} h_\uparrow^{(m)} + U^{(u)}s + b_\uparrow^{(u)})$$

$$c_\uparrow = i_\uparrow \odot u_\uparrow + \Sigma_{m=1}^M f_\uparrow^{(m)} \odot c_\uparrow^{(m)}$$

$$h_\uparrow = o_\uparrow \odot \tan h(c_\uparrow) \quad \text{(Eq. 3)}$$

where s is the SLSTM hidden state that encodes the name of the concept C. $\{h_\uparrow^{(m)}\}_{m=1}^M$ and $\{c_\uparrow^{(m)}\}_{m=1}^M$ are the bottom-up TLSTM hidden states and memory cells of the children.

W, U, b are component-specific weight matrices and bias vectors. For a leaf node having no children, its only input is the SLSTM hidden state s and no forget gates are needed. The transition equations are:

$$i_\uparrow = \sigma(U^{(i)}s + b_\uparrow^{(i)})$$

$$o_\uparrow = \sigma(U^{(o)}s + b_\uparrow^{(o)})$$

$$u_\uparrow = \tan h(U^{(u)}s + b_\uparrow^{(u)})$$

$$c_\uparrow = i_\uparrow \odot u_\uparrow$$

$$h_\uparrow = o_\uparrow \odot \tan hc_\uparrow \quad \text{(Eq. 4)}$$

In the top-down TLSTM, for a non-root node, it has the following components: an input gate $i_\downarrow$, a forget gate $f_\downarrow$, an output gate $o_\downarrow$, a memory cell $c_\downarrow$, and a hidden state $h_\downarrow$. The transition equations are:

$$i_\downarrow = \sigma(W_\downarrow^{(i)} h_\downarrow^{(p)} + v_\downarrow^{(i)})$$

$$f_\downarrow = \sigma(W_\downarrow^{(f)} h_\downarrow^{(p)} + b_\downarrow^{(f)})$$

$$o_\downarrow = \sigma(W_\downarrow^{(o)} h_\downarrow^{(p)} + b_\downarrow^{(o)})$$

$$u_\downarrow = \tan h(W^{(u)} h_\downarrow^{(p)} + b_\downarrow^{(u)})$$

$$c_\downarrow = i_\downarrow \odot u_\downarrow + f_\downarrow \odot c_\downarrow^{(p)}$$

$$h_\uparrow = o_\downarrow \odot \tan h(c_\downarrow), \quad \text{(Eq. 5)}$$

where $h_\downarrow^{(p)}$ and $c_\downarrow^{(p)}$ are the top-down TLSTM hidden state and memory cell of the parent of this node. For the root node which has no parent, $h_\downarrow$ cannot be computed using the above equations. Instead, we set $h_\downarrow$ to $h_\uparrow$ (the bottom-up TLSTM hidden state generated at the root node). $h_\uparrow$ captures the semantics of all codes, which is then propagated downwards to each individual code via the top-down TLSTM dynamics The hidden states of the two directions are concatenated to obtain the bidirectional TLSTM encoding of each concept $h = [h_\uparrow; h_\downarrow]$. The bottom-up TLSTM composes the semantics of children (representing sub-codes) and merges them into the current node, which hence captures child-to-parent relationship. The top-down TLSTM makes each node inherit the semantics of its parent, which captures parent-to-child relation. As a result, the hierarchical relationship among codes is encoded in the hidden states.

Adversarial Multi-Label Tagging Module

It is often the case that a medical image can be tagged with multiple medical concepts that exhibit clinical or biological correlations. These correlations can be leveraged to distinguish concepts that are difficult to be differentiated using visual clues. The system disclosed herein uses an adversarial learning approach to capture such correlations for better multi-label tagging. Example of adversarial learning are described in Ian Goodfellow, Jean Pouget-Abadie, Mehdi Mirza, Bing Xu, David Warde-Farley, Sherjil Ozair, Aaron Courville, and Yoshua Bengio. Generative adversarial nets. In Advances in neural information processing systems, pages 2672-2680, 2014, the disclosure of which is hereby incorporated by reference.

Figure 6:
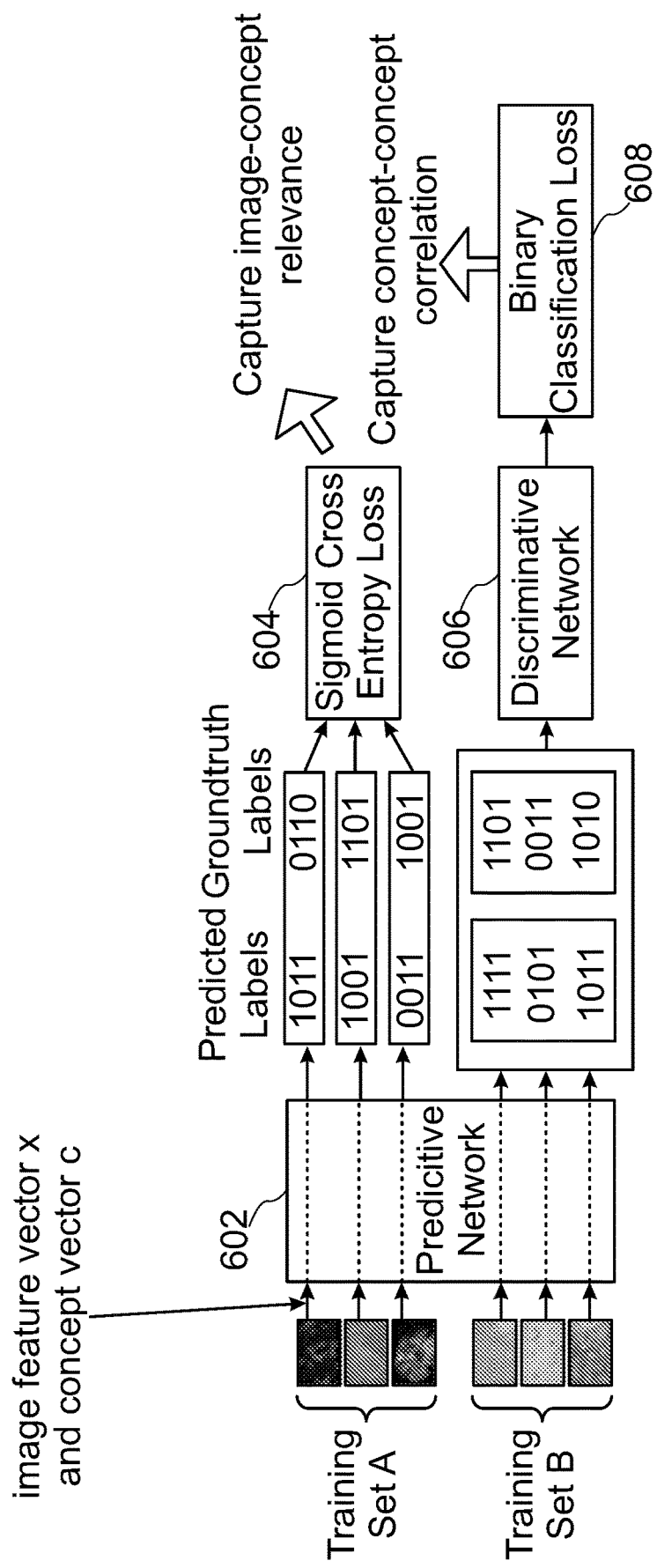
FIG. 6 is a block diagram of image and semantics processing performed by an adversarial multi-label tagging module included in the model of FIG. 2.

With reference to FIG. 6, when assigning multiple concepts to an image, two orthogonal factors: (1) concept-image relevance and (2) concept-concept correlation need to be considered. Concept-image relevance reflects how the content of the image is relevant to each concept. Concept-concept correlation reflects how strongly these concepts are correlated.

To achieve concept-image relevance, a predictive network 602 takes the representation of the image in the form of an image feature vector x produced by the visual feature module 202 or contextual attention encoder, and the representation of the concept ontology in the form of a concept vector $c_i$ of each concept i produced by the semantics module 204 or the tree-of-sequences LSTM encoder as inputs and calculates a relevance score $s_i$ that measures how relevant this image is to this concept.

Adversarial learning is used to achieve concept-concept correlation. The basic idea is to use a discriminative network 606 to tell which concepts or labels are produced by the predictive network 602 and which concepts or labels are ground truth, i.e., provided by the physicians. The predictive network 602 tries to produce labels in a way that the discriminative network 606 cannot tell whether they are predicted or ground truth. Such indiscriminability transfers the correlations manifested in ground truth labels into those predicted by the predictive network 602.

With continued reference to FIG. 6, a training set of medical images and concept ontologies is divided into two sets: A and B. Set A is used for learning the relevance between images and concepts. Set B is used for learning the correlation among concepts. The ground truth tagging of each image is represented by a binary vector $t \in \mathbb{R}^k$ where k is the number of unique leaf concepts in the ontology and $t_i = 1$ denotes that the i-th concept is utilized by the physician to label this image. For each image x in training set A, the predictive network 602 predicts a relevance score vector $s = f_P(x; W_P)$, where $s_i \in [0,1]$ denotes the confidence that this image should be tagged by concept i and $f_P(\cdot; W_P)$ denotes the predictive network parameterized by weight parameters $W_P$. Then a sigmoid cross entropy loss 604 is defined on s and t to measure the discrepancy between the prediction and the ground truth.

For each image in training set B, similarly the predictive network 602 first generates the relevance score vector s. A discriminative network 606 differentiates the predicted score vectors $\{s^{(n)}\}_{n=1}^{N_B}$ and the ground truth label vectors $\{t^{(n)}\}_{n=1}^{N_B}$ where $N_B$ is the number of images in B. This is a binary classification 608 task. The input to the discriminative network 606 (denoted by $f_D(\cdot; W_D)$ where $W_D$ are the weight parameters) is a k-dimensional vector and the output is the probability that the vector is predicted. As for the predictive network 602, it aims at making $\{s^{(n)}\}_{n=1}^{N_B}$ indistinguishable from $\{t_{(n)}\}_{n=1}^{N_B}$, such that the correlations reflected in $\{t_{(n)}\}_{n=1}^{N_B}$ can be transferred to $\{s^{(n)}\}_{n=1}^{N_B}$. Overall, the following optimization problem is solved:

$$\min_{W_P} \mathcal{L}_{SCE}(W_P, A) + \max_{W_D} -\mathcal{L}_{BC}(W_P, W_D, B). \quad \text{(Eq. 6)}$$

where $\mathcal{L}_{SCE}(W_P, A)$ is the sigmoid cross-entropy loss defined on the training set A:

$$\mathcal{L}_{SCE}(W_P, A) = \Sigma_{n=1}^{N_A} l(f_P(x^{(n)}; W_P), x^{(n)}), \quad \text{(Eq. 7)}$$

where $l(s, t) = -\Sigma_{i=1}^{k} t_i \log s_i + (1-t_i) \log(1-s_i)$ is the SCE loss on a single image and $N_A$ is the number of images in A. $\mathcal{L}_{BC}(W_P, W_D, B)$ is the binary classification loss defined on training set B:

$$\mathcal{L}_{BC}(W_P, W_D, B) = \Sigma_{n=1}^{2N_B} l(f_D(a^{(n)}; W_D), b^{(n)}) \quad \text{(Eq. 8)}$$

where $a^{(n)}$ can be either a predicted score vector $f_P(x; W_P)$ or a physician-provided label vector t. In the former case, b=1. In the latter case, b=0.

In the overall loss, the predictive network 602 learns its weight parameters $W_P$ by minimizing the sigmoid cross entropy loss and maximizing the binary classification loss 608. The discriminative network 606 learns its weights parameters $W_D$ by minimizing the binary classification loss. Note that the sigmoid cross entropy loss and the binary classification loss cannot be defined on the same training image. By overfitting the training set, the sigmoid cross entropy loss can make the predicted label vector to be the same as the ground truth vector.

Previously, adversarial learning was applied for domain adaptation: a discriminator is learned to judge whether an example is from the source domain or target domain; an encoder is learned so that after being encoded, a sample cannot be identified as being from the source domain or target domain. By doing this, the discrepancy between two domains are eliminated so that data from the source domain can be utilized to improve the task in the target domain. In the disclosed system's use of adversarial learning for multi-label classification, a similar idea is explored: using adversarial learning to eliminate the discrepancy between the predicted labels and ground-truth labels in terms of label-correlation patterns, so that the correlations existing in the ground-truth labels can be transferred to the predicted labels.

The model for training the machine-learned algorithm disclosed herein includes an adversarial multi-label tagging mechanism 206 that implements an adversarial learning approach where a discriminative network 606 is used to distinguish predicted labels or tags for an image from ground truth or physician-provided labels while a predictive network 602 tries to make them indistinguishable (i.e., cannot tell whether a label vector is predicted or human-provided). Such indiscernibility ensures the correlations among physician-provided tags are transferred to the predicted tags. The model also includes a semantics mechanism 204 that employs a LSTM model which uses sequential LSTMs to encode the individual concepts and a tree-structured LSTM to capture the hierarchical relationship among concepts. A contextual attention mechanism 202 calculates an importance score or attention score 314 of each image-patch according to its contrast with the entire image. Patches with larger importance scores are paid more attention in predicting the tags.

Text Report Generation Module

With reference to FIG. 2, the machine-learned algorithm 110 may also include a text report generation module 216 configured to generate a complete diagnostic report for a medical image that includes both unstructured descriptions (in the form of sentences and paragraphs) and semi-structured tags (in the form of keyword lists). To this end, a multi-task hierarchical model with co-attention automatically predicts keywords and generate long paragraphs.

Figure 7:
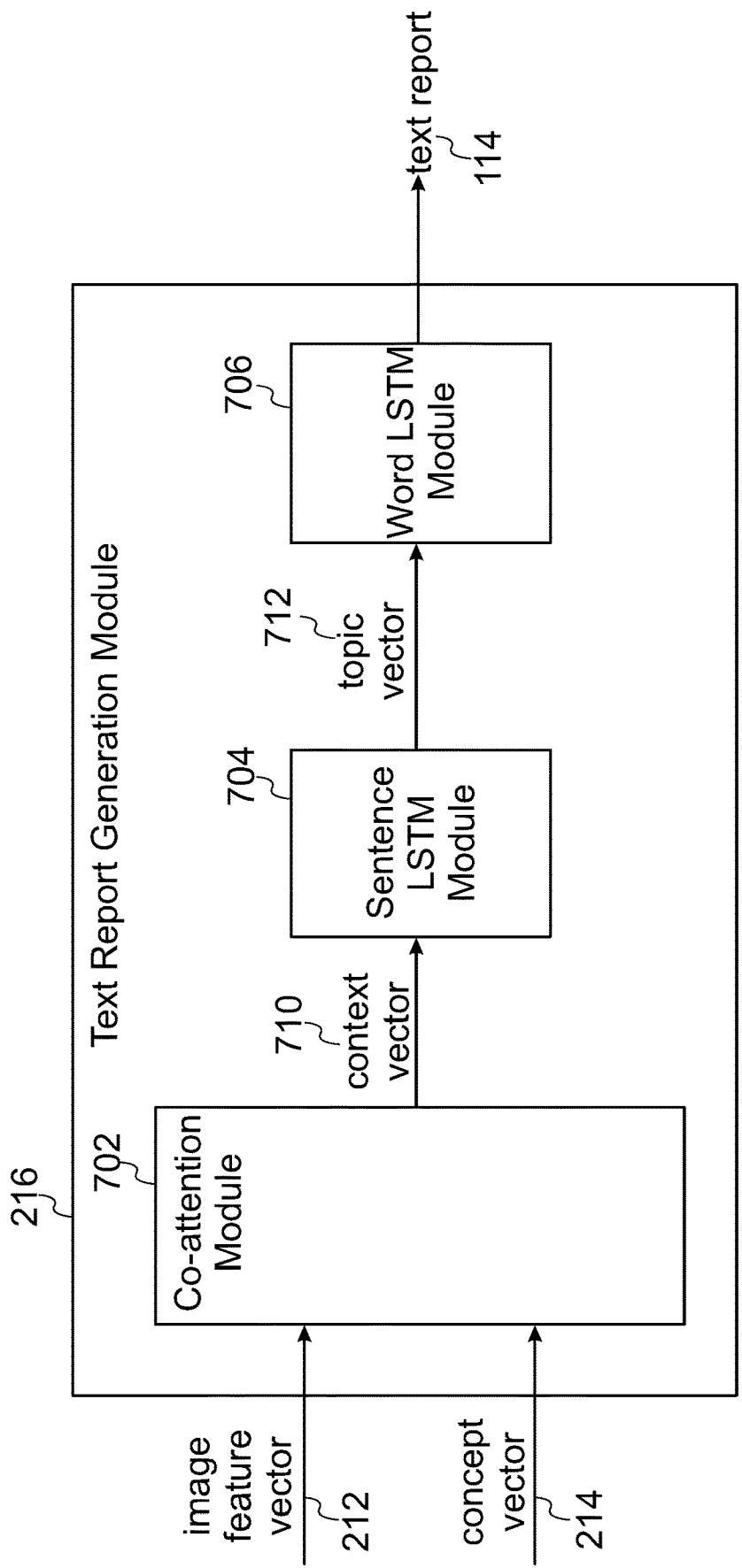
FIG. 7 is a block diagram of image and semantics processing performed by a text report generation module included in the model of FIG. 2.

With reference to FIG. 7, the text report generation module 216 includes a co-attention module 702, a sentence LSTM module 704, and a word LSTM module 706. The inputs to the co-attention module 702 may correspond to the image feature vectors 212 and the concept vectors 214 described above with reference to FIGS. 2-5. The co-attention module 702 generates a context vector 710 that simultaneously captures the visual and semantic information of this image. The co-attention module 702 may be configured the same as the adversarial multi-label tagging module 206 described above with reference to FIGS. 2 and 6.

Next, starting from the context vector 710, the decoding process generates the text descriptions. The description of a medical image usually contains multiple sentences, and each sentence focuses on one specific topic. The text report generation module 216 leverages this compositional structure to generate reports in a hierarchical way. To this end, the sentence LSTM module 704 and the word LSTM module 706 function together to generate 1) a sequence of high-level topic vectors representing sentences, and then 2) a sentence (a sequence of words) from each topic vector. Specifically, the context vector 710 is inputted into the sentence LSTM module 704, which unrolls for a few steps, each step producing a topic vector 712. A topic vector 712 represents the semantics of a sentence to be generated. Given a topic vector 712, the word LSTM module 706 takes it as input and generates a sequence of words to form a sentence. The termination of the unrolling process is controlled by the sentence LSTM module 704.

With reference to FIG. 8, examples of medical images and corresponding text reports generated under different scenarios are shown. The ground truth reports in the first column are written by physicians. The text reports shown in the second column are reports generated by the text report generation module 216 disclosed herein.

Figure 9:
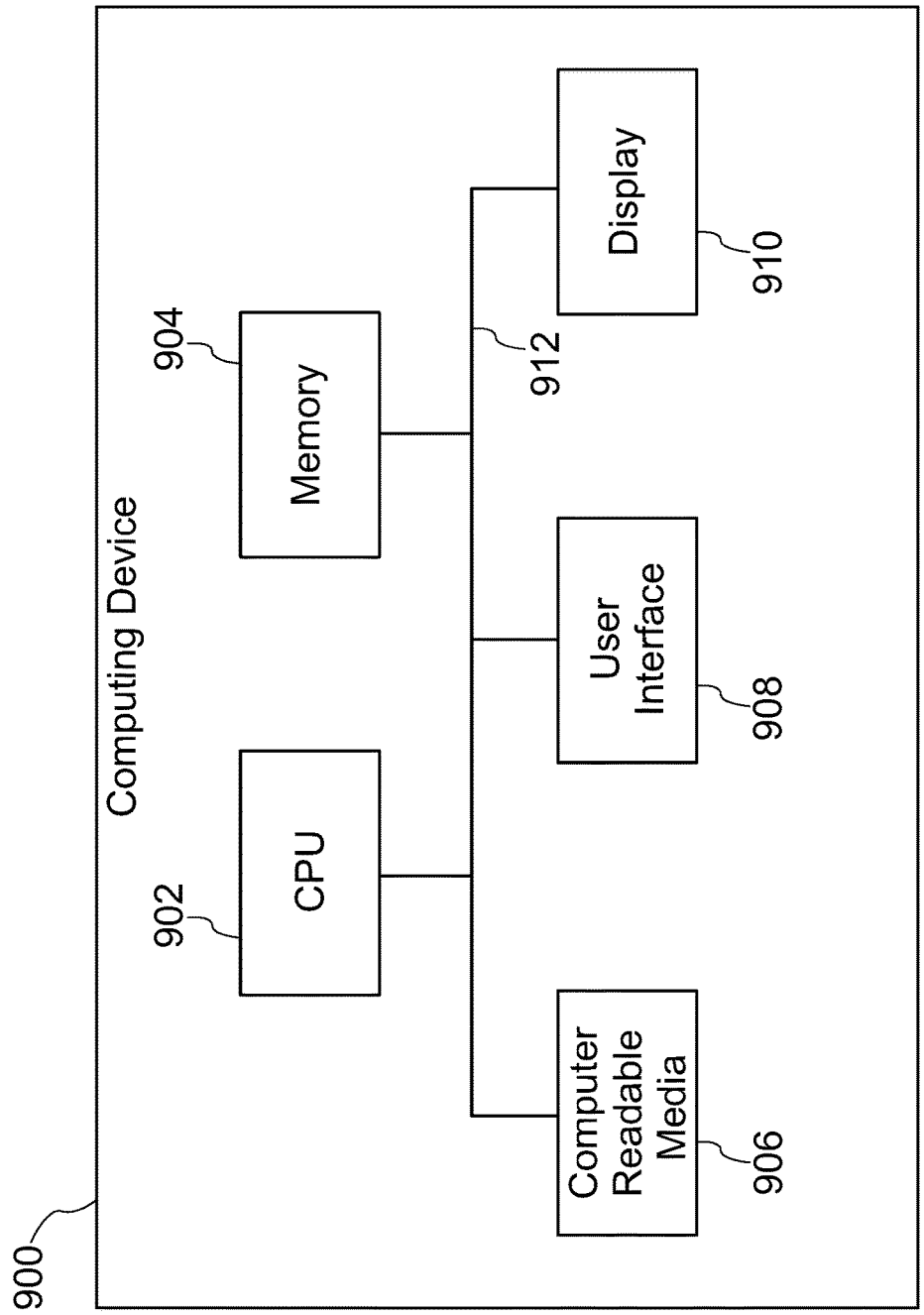
FIG. 9 is a block diagram of a computing device that embodies the system of FIG. 1.

FIG. 9 is a block diagram of a computing device 900 that embodies the medical image tagging system 100 of FIG. 1. The computing device 900 is specially configured to execute instructions related to the concept tagging and text report generation process described above, including the application of machine-learned algorithms to medical images. Computers capable of being specially configured to execute such instructions may be in the form of a laptop, desktop, workstation, or other appropriate computers.

The computing device 900 includes a central processing unit (CPU) 902, a memory 909, e.g., random access memory, and a computer readable media 906 that stores program instructions that enable the CPU and memory to implement the functions of the visual feature module 102 and the tagging module 104 of the medical image tagging system 100 described above with reference to FIG. 1. The computing device 900 also includes a user interface 908 and a display 910, and an interface bus 912 that interconnects all components of the computing device.

Computer readable media 906 is suitable for storing medical image tagging system processing instructions include all forms of non-volatile memory, media and memory devices, including by way of example semiconductor memory devices, flash memory devices, magnetic disks, magneto optical disks and CD ROM and DVD-ROM disks. In operation, the CPU 902 and memory 909 executes the medical image tagging system processing instructions stored in the computer readable media 906 to thereby perform the functions of the visual feature module 102 and the tagging module 104.

The user interface 908, which include an image scanner and one or more of a keyboard or a mouse, and the display 910 allow for a clinician to interface with the computing device 900. For example, a clinician seeking to obtain key concepts for a medical image or a text report describing a medical image, may input the medical image for processing through the image scanner. The clinician may then initiate execution of the medical image tagging system processing instructions stored in the computer readable media 906 through the user interface 908, and await a display of the key concepts and/or text report.

Figure 10:
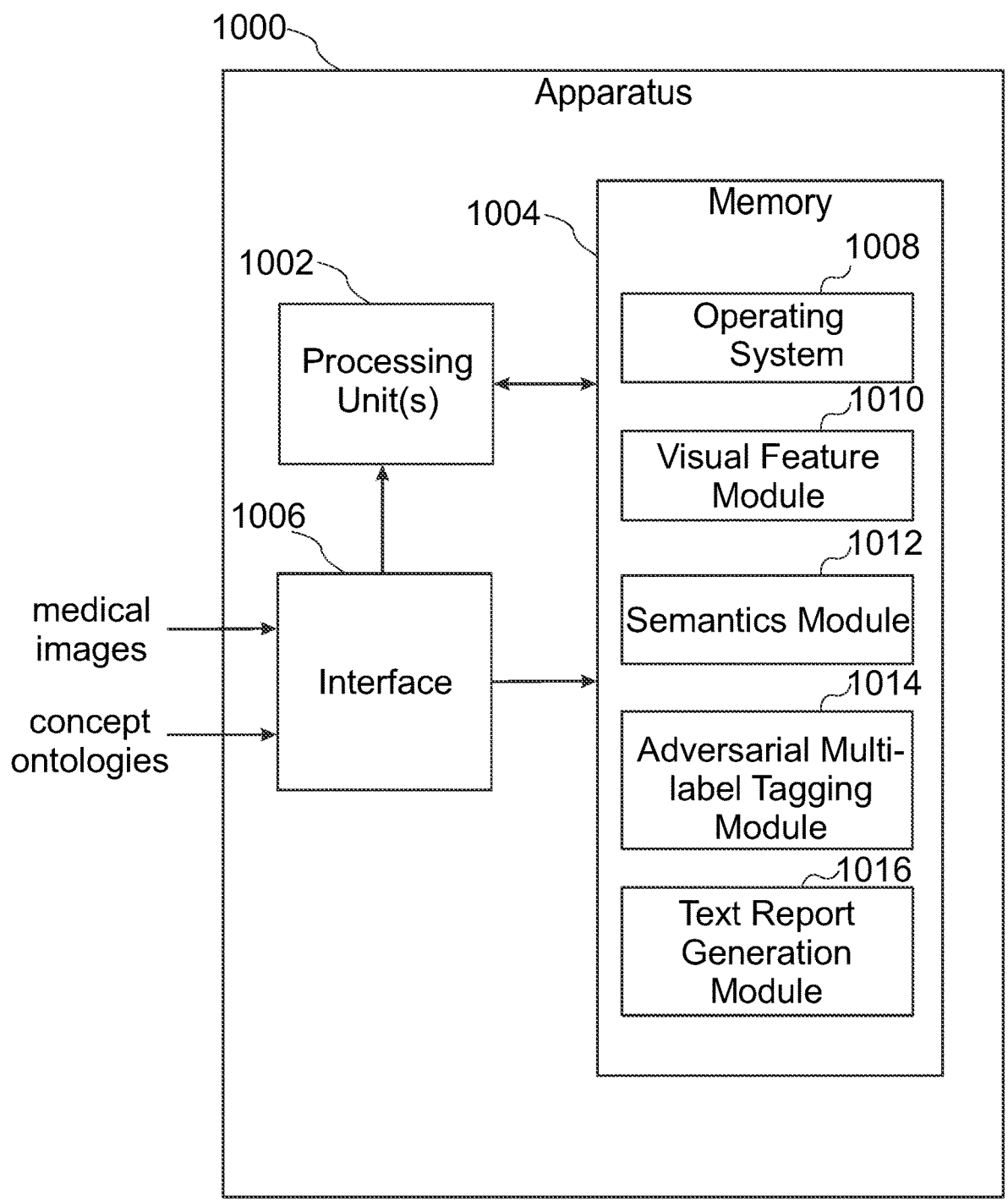
FIG. 10 is a block diagram of an apparatus that develops and trains the machine-learned algorithm of FIG. 1.
Figure 11A:
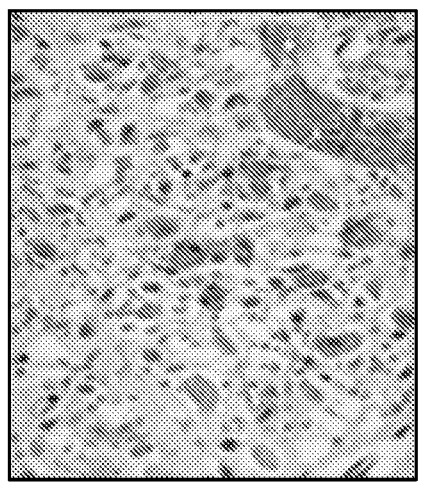
FIG. 11A is an example medical image having multiple tags that are correlated clinically or biologically with the image.
Figure 11B:
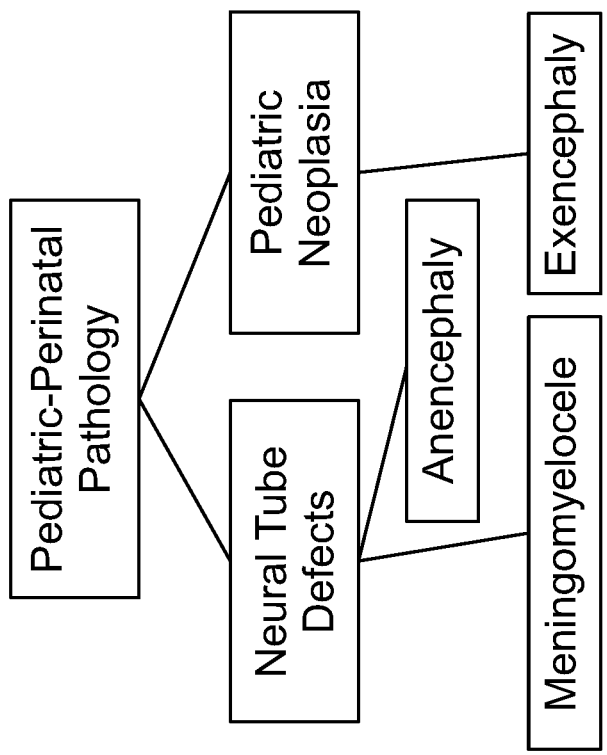
FIG. 11B is an illustration of medical concepts organized into a hierarchical tree.
Figure 11C:
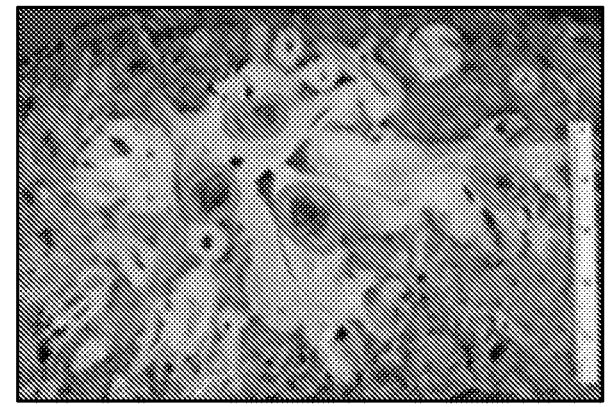
FIG. 11C is an example of a medical image having abnormal regions marked by circular contours.

FIG. 10 is a schematic block diagram of an apparatus 1000. The apparatus 1000 may correspond to one or more processors configured to develop and train the machine-learned algorithm included in the medical image tagging system 100 of FIG. 1 in accordance with the model of FIG. 2. The apparatus 1000 may be embodied in any number of processor-driven devices, including, but not limited to, a server computer, a personal computer, one or more networked computing devices, an application-specific circuit, a minicomputer, a microcontroller, and/or any other processor-based device and/or combination of devices.

The apparatus 1000 may include one or more processing units 1002 configured to access and execute computer-executable instructions stored in at least one memory 1004. The processing unit 1002 may be implemented as appropriate in hardware, software, firmware, or combinations thereof. Software or firmware implementations of the processing unit 1002 may include computer-executable or machine-executable instructions written in any suitable programming language to perform the various functions described herein. The processing unit 1002 may include, without limitation, a central processing unit (CPU), a digital signal processor (DSP), a reduced instruction set computer (RISC) processor, a complex instruction set computer (CISC) processor, a microprocessor, a microcontroller, a field programmable gate array (FPGA), a System-on-a-Chip (SOC), or any combination thereof. The apparatus 1000 may also include a chipset (not shown) for controlling communications between the processing unit 1002 and one or more of the other components of the apparatus 1000. The processing unit 1002 may also include one or more application-specific integrated circuits (ASICs) or application-specific standard products (ASSPs) for handling specific data processing functions or tasks.

The memory 1004 may include, but is not limited to, random access memory (RAM), flash RAM, magnetic media storage, optical media storage, and so forth. The memory 1004 may include volatile memory configured to store information when supplied with power and/or non-volatile memory configured to store information even when not supplied with power. The memory 1004 may store various program modules, application programs, and so forth that may include computer-executable instructions that upon execution by the processing unit 1002 may cause various operations to be performed. The memory 1004 may further store a variety of data manipulated and/or generated during execution of computer-executable instructions by the processing unit 1002.

The apparatus 1000 may further include one or more interfaces 1006 that may facilitate communication between the apparatus and one or more other apparatuses. For example, the interface 1006 may be configured to receive medical images and concept ontologies. Communication may be implemented using any suitable communications standard. For example, a LAN interface may implement protocols and/or algorithms that comply with various communication standards of the Institute of Electrical and Electronics Engineers (IEEE), such as IEEE 802.11, while a cellular network interface implement protocols and/or algorithms that comply with various communication standards of the Third Generation Partnership Project (3GPP) and 3GPP2, such as 3G and 4G (Long Term Evolution), and of the Next Generation Mobile Networks (NGMN) Alliance, such as 10G.

The memory 1004 may store various program modules, application programs, and so forth that may include computer-executable instructions that upon execution by the processing unit 1002 may cause various operations to be performed. For example, the memory 1004 may include an operating system module (O/S) 1008 that may be configured to manage hardware resources such as the interface 1006 and provide various services to applications executing on the apparatus 1000.

The memory 1004 stores additional program modules such as: (1) a visual feature module that receives medical images and generates attentional representations of the images in the form of encoded image feature vectors; (2) an semantics module 1012 that receives concept ontologies of the medical images and generates representations of the concepts in the form of encoded concept vectors; (3) an adversarial multi-label tagging module 1014 that maps concepts with images; and (4) a text report generation module 1016 that generate written reports describing medical images. Each of these modules includes computer-executable instructions that when executed by the processing unit 1002 cause various operations to be performed, such as the operations described above.

The apparatus 1000 and modules disclosed herein may be implemented in hardware or software that is executed on a hardware platform. The hardware or hardware platform may be a general purpose processor, a digital signal processor (DSP), an application specific integrated circuit (ASIC), a field programmable gate array (FPGA) or other programmable logic component, discrete gate or transistor logic, discrete hardware components, or any combination thereof, or any other suitable component designed to perform the functions described herein. A general-purpose processor may be a microprocessor, but in the alternative, the processor may be any conventional processor, controller, microcontroller, or state machine. A processor may also be implemented as a combination of computing components, e.g., a combination of a DSP and a microprocessor, a plurality of microprocessors, one or more microprocessors in conjunction with a DSP, or any other such configuration.

Evaluation

We used two medical image datasets obtained from a teaching hospital. The first dataset contains 47933 pathology images which are split into a training set with 33553 images, a validation set with 7190 images, and a test set with 7190 images. The second dataset contains 39827 radiology images, which are split into train/validation/test sets with 27879, 5974, and 5974 images respectively. Labels in the first dataset are organized by doctors into a 4-level hierarchy. The number of labels in level 1-4 are 16, 38, 137, 249 respectively. The number of leaf nodes is 272. The aver-age labels each image has is 3.7. Each label has a name. The minimum, average, and maximum number of words in the label names are 1, 5.3, 9 respectively. Labels in the second dataset are organized by doctors into a 3-level hierarchy. The number of labels in level 1-3 are 12, 51, 196 respectively. The number of leaf nodes is 211. The average labels each image has is 3.1. The minimum, average, and maximum number of words in the label names are 1, 4.4, 8 respectively. Each image is labeled by at least 3 doctors and the labels are decided using majority vote. The kappa statistics (range is [−1,1]) for measuring inter-annotator reliability is 0.83, indicating high consistency among annotators. Since it is too costly to annotate fine-grained hierarchical labels for all raw images in the PACS, we did not use all images there. The distribution of classes' frequencies is imbalanced: some classes appear in many images while others are less frequent. The number of tags that each image has follows a Gaussian distribution.

Experimental Setup: Data augmentation by cropping and rotating was applied. The images were resized to 3000× 2000. Each image was divided into 16×16 overlapping patches with a stride of 8. In the contextual attentional encoder, both the image encoder and patch encoder were set to ResNet-50, where the 1000-dimensional vector produced by the fully-connected layer is used as the representation of an image or a patch. The attention module was a feed-forward network with 2 hidden layers where the number of unit was 300 and 100 respectively. The activation function was set to ReLU. The attentional encoder was also set to ResNet-50. In the tree-of-sequences LSTM encoder, the hidden state size of both the sequential and tree-structured LSTM was set to 100. The size of word embedding was set to 128. In the adversarial multi-label tagger, 70% training images were used as set A to learn label-image relevance. The rest were used as set B to learn label-correlations. Both the predictive and discriminative networks were feed-forward networks with 2 hidden layers where the number of units was 300 and 100 respectively. We used Ada-Grad with a learning rate of 0.1 and batch size of 32 to learn model parameters. In LSTM training, the network was unrolled for 60 iterations. For performance evaluation, we used sensitivity (true positive rate) and specificity (true negative rate), which are the most widely used evaluation metrics in clinical trial. To address the imbalance issue of classes' frequency, in the loss function in Eq. 7, we gave infrequent classes larger weights, where the weight of a class is proportional to the reciprocal of the frequency of this class.

Ablation Study: We perform ablation study to verify the effectiveness of each module.

Adversarial learning for multi-label tagging: To evaluate the efficacy of adversarial learning (AL), we removed it from the model. In FIG. 6, the branch associated with training set B (including the discriminative network and binary classification loss) was taken away. All the training images were put into set A to learn label-image relevance. In addition, we compared with four state of the art methods proposed for capturing label-correlation in multi-label classification by replacing AL with each of them while keeping the other modules intact. These baselines include (1) conditional random field (CRF); (2) structured prediction energy net-work (SPEN); (3) CNN-RNN; (4) determinantal point process (DPP). In SPEN, The local and global energy networks are chosen to be feed-forward networks consisting of two hidden layers, with 300 and 150 units in each layer. Gradient descent was applied to make predictions, where the momentum and learning rate were set to 0.95 and 0.01 respectively. In CNN-RNN, the size of hidden states in LSTM was set to 128. The network was trained using SGD with momentum 0.9, weight decay 1e-4, and dropout rate 0.5. In the DPP baseline, we feed the image representation produced by the contextual attention encoder and concept representations produced by the tree-of-sequence LSTM encoder into a conditional kernel function represented by a label-input dependency network (LIDN) and a label-correlation network (LCN). The LIDN is configured to be a fully-connected network with 2 hidden layers where the number of units in the first and second layer is 200 and 100 respectively and the activation function is ReLU. The LCN has two hidden layers as well, each having 100 and 50 units respectively.

The first panel of Table 1 shows the results. On the first, second, and third panel are baselines compared in the ablation study of (1) adversarial learning for multi-label tagging, (2) tree-of-sequences LSTM for capturing hierarchical relationship, and (3) contextual attention for identifying abnormalities. On the fourth panel are baselines for holistic comparison. From these results we observe the following. First, after AL is removed (denoted by No-AL), the sensitivity and specificity are significantly dropped. No-AL ignores label-correlations and selects labels purely based on their relevance to the image, hence leading to inferior performance.

TABLE 1

| Methods | Pathology | | Radiology | |
| --- | --- | --- | --- | --- |
| | Sensitivity | Specificity | Sensitivity | Specificity |
| CRF | 0.30 | 0.34 | 0.48 | 0.50 |
| SPEN | 0.32 | 0.34 | 0.46 | 0.48 |
| CNN-RNN | 0.31 | 0.35 | 0.48 | 0.51 |
| DPP | 0.32 | 0.34 | 0.47 | 0.49 |
| No-AL | 0.30 | 0.33 | 0.46 | 0.48 |
| LET | 0.30 | 0.35 | 0.48 | 0.50 |
| HD-CNN | 0.31 | 0.35 | 0.46 | 0.49 |
| HybridNet | 0.32 | 0.36 | 0.45 | 0.49 |
| B-CNN | 0.30 | 0.34 | 0.48 | 0.51 |
| No-TLSTM | 0.29 | 0.34 | 0.45 | 0.49 |
| Bottom-up TLSTM | 0.33 | 0.36 | 0.48 | 0.51 |
| LPA | 0.30 | 0.35 | 0.50 | 0.51 |
| SA | 0.31 | 0.35 | 0.49 | 0.49 |
| No-CA | 0.30 | 0.34 | 0.48 | 0.49 |
| DTHMLC | 0.20 | 0.23 | 0.39 | 0.40 |
| DenseNet-LSTM | 0.27 | 0.29 | 0.44 | 0.46 |
| OS | 0.22 | 0.23 | 0.41 | 0.44 |
| Our full method | 0.33 | 0.37 | 0.50 | 0.52 |

Second, compared with the four baselines designed for capturing label-correlations, our full method (which uses AL) achieves better performance, suggesting that AL is more effective in capturing correlations. These baselines design explicit objective functions to encode correlations. The correlations might be very complicated and diverse, which are difficult to be captured by a single objective function. Instead, our approach implicitly learns such correlation by making the predicted labels indistinguishable from the ground truth ones. It has more flexibility and expressivity to capture various types of correlations. The ad-vantage of DPP is that it is able to capture high-order correlations among labels while being able to perform the exact learning of model parameters (without approximation) with cubic computational complexity (in terms of the number of unique classes). Its drawback is exact inference cannot be achieved in polynomial time. Approximate inference may bear large errors. The disadvantage of CRF is both inference and parameter learning cannot be performed exactly.

Tree-of-sequences LSTM: To evaluate this module, we compared with the two configurations: (1) No TLSTM, which removes the tree LSTM and directly uses the hidden states produced by the sequential LSTM as final representations of concepts; (2) Bottom-up TLSTM, which removes the hidden states generated by the top-down TLSTM. In addition, we compared with four hierarchical classification baselines including (1) hierarchical deep CNN (HD-CNN), (2) HybridNet, (3) Branch CNN (B-CNN), (4) label embedding tree (LET), by using them to replace the bidirectional tree LSTM while keeping other modules untouched. The second panel of Table 1 shows the sensitivity and specificity achieved by these methods. We make the following observations. First, removing tree LSTM (No TLSTM) greatly degrades performance since the hierarchical relationship among labels is ignored. Second, the bottom-up tree LSTM alone performs less well than our full method that uses the bi-directional tree LSTM. This demonstrates the necessity of the top-down TLSTM, which ensures every two labels are connected by directed paths and can more expressively capture label-relations in the hierarchy. Third, our full method outperforms the four baselines. The possible reason is that our method directly builds labels' hierarchical relationship into their representations while the baselines perform representation-learning and relationship-capturing separately.

Contextual attention: In the evaluation of this module, we compared with No-CA which re-moves the contextual attention (CA) module, and two other attention models: (1) label-patch attention (LPA); (2) scale attention (SA). The third panel of Table 1 shows the performance scores achieved by these methods. As can be seen, the sensitivity and specificity under No-CA is lower than our full method which uses CA, which demonstrates the effectiveness of contextual attention. CA is able to localize the small abnormal regions and pays more attention to them, which leads to the successful tagging of abnormalities. Compared with other attention baselines, our full method with CA achieves better performances. This indicates that for medical images, the contextual information embodied in the entire image is very valuable for distilling "attention".

We asked doctors to label the abnormal regions in 100 pathology and 100 radiology images. We compared the abnormal regions detected by our contextual attention model with the ground truth using Intersection over Union (IoU). We evaluated how patch size affects performance. Table 2 shows IoU and sensitivity/specificity of tagging under different patch sizes (the stride size is set to 8).

TABLE 2

|  |  | Pathology | | | Radiology | | |
| --- | --- | --- | --- | --- | --- | --- | --- |
|  | Size | IoU | Sensitivity | Specificity | IoU | Sensitivity | Specificity |
| Patch | 8 | 0.25 | 0.32 | 0.36 | 0.40 | 0.47 | 0.49 |
|  | 16 | 0.29 | 0.33 | 0.37 | 0.41 | 0.49 | 0.50 |
|  | 32 | 0.28 | 0.32 | 0.34 | 0.43 | 0.50 | 0.52 |
|  | 64 | 0.24 | 0.30 | 0.31 | 0.39 | 0.47 | 0.48 |
| Stride | 4 | 0.28 | 0.30 | 0.37 | 0.40 | 0.48 | 0.51 |
|  | 8 | 0.29 | 0.33 | 0.37 | 0.43 | 0.50 | 0.52 |
|  | 16 | 0.27 | 0.31 | 0.36 | 0.42 | 0.47 | 0.50 |

As can be seen, a patch size in the middle ground (that best matches the scale of abnormal regions) yields the best abnormality detection and tagging performance. We also evaluated how the stride size in overlapping patches affects performance. Fixing the patch size to 16, we tried stride sizes of 4, 8, and 16 (equivalent to nonoverlap). As can be seen from the table, overlap with a stride size 8 works better than nonoverlap.

Holistic comparison with other baselines: In addition to evaluating the three modules individually, we also compared the entire model with three other baselines, including (1) decision trees for hierarchical multi-label classification (DTHMLC), (2) DenseNet-LSTM designed in for chest x-ray classification, (3) Occlusion sensitivity (OS) used in for abnormality localization in x-rays.

The fourth panel of Table 1 shows the comparison with these baselines. As can be seen, our approach achieves much better performances on both datasets than the baselines. DTHMLC performs less well probably because it lacks the ability to learn deep visual features. DenseNet-LSTM lacks the ability to explore concept-hierarchy. OS cannot be trained in an end-to-end fashion which leads to inferior performance.

We evaluated the effects of tagging on image search. We used the learned models to tag images in the PACS. For either pathology or radiology images, we randomly sampled 100 tags as queries, then performed retrieval by tag matching. We compared with a baseline: retrieval by checking whether the query tag is contained in the image reports. Retrieval performance was evaluated using precision@10: among the top 10 retrieved images, how many are relevant to the query (whether being relevant is labeled by doctors). The precision@10 achieved by reports-based retrieval is 0.24 for pathology and 0.32 for radiology. Our tagging method improves the precision@10 to 0.29 for pathology and 0.40 for radiology.

On the pathology dataset, our method is significantly better than CRF, No-AL, LET, B-CNN, No-TLSTM, LPA, No-CA, DTHMLC, DenseNet-LSTM, OS with p-value <0.01, and is significantly better than SPEN, CNN-RNN, DPP, HD-CNN, HybridNet, SA with p-value<0.05. On the pathology dataset, our method is significantly better than SPEN, DPP, No-AL, HD-CNN, HybridNet, No-TLSTM, No-CA, DTHMLC, DenseNet-LSTM, OS with p-value<0.01, and is significantly better than CRF, CNN-RNN, LET, B-CNN, Bottom-up TLSTM, SA with p-value<0.05.

Software shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise. The software may reside on a computer-readable medium. A computer-readable medium may include, by way of example, a magnetic storage device (e.g., hard disk, floppy disk, magnetic strip), an optical disk (e.g., compact disk (CD), digital versatile disk (DVD)), a smart card, a flash memory device (e.g., card, stick, key drive), random access memory (RAM), read only memory (ROM), programmable ROM (PROM), erasable PROM (EPROM), electrically erasable PROM (EEPROM), a general register, or any other suitable non-transitory medium for storing software.

While various embodiments have been described above, they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations.

In this document, the terms "module" and "engine" as used herein, refers to software, firmware, hardware, and any combination of these elements for performing the associated functions described herein. Additionally, for purpose of discussion, the various modules are described as discrete modules; however, as would be apparent to one of ordinary skill in the art, two or more modules may be combined to form a single module that performs the associated functions according embodiments of the invention.

In this document, the terms "computer program product", "computer-readable medium", and the like, may be used generally to refer to media such as, memory storage devices, or storage unit. These, and other forms of computer-readable media, may be involved in storing one or more instructions for use by processor to cause the processor to perform specified operations. Such instructions, generally referred to as "computer program code" (which may be grouped in the form of computer programs or other groupings), when executed, enable the computing system.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "normal," "standard," "known", and terms of similar meaning, should not be construed as limiting the item described to a given time period, or to an item available as of a given time. But instead these terms should be read to encompass conventional, traditional, normal, or standard technologies that may be available, known now, or at any time in the future.

Additionally, memory or other storage, as well as communication components, may be employed in embodiments of the invention. It will be appreciated that, for clarity purposes, the above description has described embodiments of the invention with reference to different functional units and processors. However, it will be apparent that any suitable distribution of functionality between different functional units, processing logic elements or domains may be used without detracting from the invention. For example, functionality illustrated to be performed by separate processing logic elements or controllers may be performed by the same processing logic element or controller. Hence, references to specific functional units are only to be seen as references to suitable means for providing the described functionality, rather than indicative of a strict logical or physical structure or organization.

Furthermore, although individually listed, a plurality of means, elements or method steps may be implemented by, for example, a single unit or processing logic element. Additionally, although individual features may be included in different claims, these may possibly be advantageously combined. The inclusion in different claims does not imply that a combination of features is not feasible and/or advantageous. Also, the inclusion of a feature in one category of claims does not imply a limitation to this category, but rather the feature may be equally applicable to other claim categories, as appropriate.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A method of assigning concepts to a medical image, the method comprising:
    obtaining an image feature vector from the medical image; and
    applying a machine-learned algorithm to the image feature vector to assign a set of concepts to the medical image, wherein the machine-learned algorithm is configured to generate a complete diagnostic report for the medical image that includes a plurality of unstructured descriptions and a plurality of semi-structured tags, wherein the machine-learned algorithm is configured to generate a context vector to capture visual and semantic information of the medical image, wherein the machine-learned algorithm predicts a plurality of keywords and generates a plurality of long paragraphs.

2. The method of claim 1, wherein the image feature vector corresponds to an attentional representation of the medical image, and obtaining the image feature vector comprises:
    obtaining an image representation for the medical image;
    obtaining a plurality of patch representations, each for a corresponding one of a plurality of patches of the medical image;
    for each of the plurality of patches:
        generating an attention score based on the image representation and the patch representation; and
        weighting image pixels of the patch based on the attention score; and generating the attentional representation corresponding to the image feature vector based on the weighted image pixels.

3. The method of claim 1, wherein applying the machine-learned algorithm to the image feature vector comprises:
    selecting one or more concepts to assign to the medical image based on a mapping function maintained in the machine-learned algorithm that maps concepts to medical images.

4. The method of claim 3, wherein the mapping function maintained in the machine-learned algorithm is trained to map concepts to medical images based on:
    measures of relevance between medical images and concepts; and
    measures of correlation among different concepts.

5. The method of claim 4, wherein the concepts are included in a concept vector obtained by processing at least one concept ontology record with a long short-term memory (LSTM) recurrent neural network.

6. The method of claim 5, wherein the LSTM is a tree-of-sequences LSTM.

7. The method of claim 1, further comprising generating a written report describing the medical image based on the set of concepts assigned to the medical image.

8. A system for assigning concepts to a medical image, the system comprising:
    a processor configured to:
        obtain an image feature vector from the medical image; and
        apply a machine-learned algorithm to the image feature vector to assign a set of concepts to the medical image, wherein the machine-learned algorithm is configured to generate a complete diagnostic report for the medical image that includes a plurality of unstructured descriptions and a plurality of semi-structured tags, wherein the machine-learned algorithm is configured to generate a context vector to capture visual and semantic information of the medical image, wherein the machine-learned algorithm predicts a plurality of keywords and generates a plurality of long paragraphs.

9. The system of claim 8, wherein the image feature vector corresponds to an attentional representation of the medical image, and the processor is further configured to obtain the image feature vector by being configured to:
   obtain an image representation for the medical image;
   obtain a plurality of patch representations, each for a corresponding one of a plurality of patches of the medical image;
   for each of the plurality of patches:
      generate an attention score based on the image representation and the patch representation; and
      weight image pixels of the patch based on the attention score; and
   generate the attentional representation corresponding to the image feature vector based on the weighted image pixels.

10. The system of claim 8, wherein the machine-learned algorithm maintains a mapping function that maps concepts to medical images and the processor is configured to select one or more concepts to assign to the medical image based on the mapping function.

11. The system of claim 10, wherein the mapping function maintained in the machine-learned algorithm is trained to map concepts to medical images based on:
   measures of relevance between medical images and concepts; and
   measures of correlation among different concepts.

12. The system of claim 11, wherein the concepts are included in an concept vector obtained by processing at least one concept ontology record with a long short-term memory (LSTM) recurrent neural network.

13. The system of claim 12, wherein the LSTM is a tree-of-sequences LSTM.

14. The system of claim 8, further comprising a text report generator configured to generate a written report describing the medical image based on the set of concepts assigned to the medical image.

15. A machine learning apparatus for generating a map between medical image concepts and medical images, the apparatus comprising:
   a processor; and
   a memory coupled to the processor; and
   wherein the processor is configured to:
      generate representations of medical images in a form of image feature vectors;
      generate representations of concepts describing medical images in a form of concept vectors;
      process the image feature vectors and the concept vectors to obtain measures of relevance between images and concepts and measures of correlation among different concepts, and
      associate each medical image represented in the image feature vector with one or more concepts represented in the concept vector based on the measures of relevance and the measures of correlation, wherein the processor is configured to generate a complete diagnostic report for the medical image by utilizing utilizes a machine-learned algorithm, wherein the medical image includes a plurality of unstructured descriptions and a plurality of semi-structured tags, wherein the machine-learned algorithm is configured to generate a context vector to capture visual and semantic information of the medical image, wherein the machine-learned algorithm predicts a plurality of keywords and generates a plurality of long paragraphs.

16. The machine learning apparatus of claim 15, wherein the image feature vectors correspond to an attentional representation of medical images, and the processor obtains the image feature vector by being configured to:
   obtain an image representation for the medical image;
   obtain a plurality of patch representations, each for a corresponding one of a plurality of patches of the medical image;
   for each of the plurality of patches:
      generate an attention score based on the image representation and the patch representation; and
      weight image pixels of the patch based on the attention score; and
   generate the attentional representation corresponding to the image feature vector based on the weighted image pixels.

17. The machine learning apparatus of claim 15, wherein the processor generates representations of concepts describing medical images in a form of concept vectors by processing at least one concept ontology record with a long short-term memory (LSTM) recurrent neural network.

18. The machine learning apparatus of claim 17, wherein the LSTM is a tree-of-sequences LSTM.

19. The machine learning apparatus of claim 15, wherein:
   a first set of image feature vectors and the concept vectors are processed to obtain the measures of relevance between images and concepts; and
   a second set, different from the first set, of image feature vectors and the concept vectors are processed to obtain the measures of correlation among different concepts.

* * * * *